United States Patent
Roe et al.

(10) Patent No.: US 6,423,044 B1
(45) Date of Patent: **\*Jul. 23, 2002**

(54) DISPOSABLE ARTICLE HAVING BODILY WASTE ISOLATION DEVICE

(75) Inventors: Donald C. Roe, West Chester, OH (US); Beth A. Rhorer, Ft. Thomas, KY (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/342,331

(22) Filed: Jun. 29, 1999

Related U.S. Application Data

(63) Continuation-in-part of application No. 09/107,561, filed on Jun. 29, 1998, now Pat. No. 6,149,636, and a continuation-in-part of application No. 09/106,225, filed on Jun. 29, 1998, now Pat. No. 6,186,991.
(60) Provisional application No. 60/090,993, filed on Jun. 29, 1998.

(51) Int. Cl.[7] .................................................. A61F 13/15
(52) U.S. Cl. .................................................. 604/385.12
(58) Field of Search .................................. 604/361, 367, 604/369, 385.01, 385.12, 385.19

(56) References Cited

U.S. PATENT DOCUMENTS

| 4,311,479 A | 1/1982 | Fenn et al. ................... 8/495 |
| 5,678,564 A | 10/1997 | Lawrence et al. .......... 128/761 |
| 6,093,869 A | * 7/2000 | Roe et al. .................... 604/361 |

FOREIGN PATENT DOCUMENTS

| JP | 01277558 | 11/1999 | ............ A61F/5/44 |
| WO | WO 94/24974 | 11/1994 | ........... A61F/13/15 |
| WO | WO 96/20681 | 7/1996 | ........... A61F/13/15 |
| WO | WO 97/32542 | 9/1997 | ............. A61F/2/00 |

* cited by examiner

*Primary Examiner*—Dennis Ruhl
(74) *Attorney, Agent, or Firm*—Jeffrey R. Moore; David M. Weirich

(57) ABSTRACT

A disposable article preferably includes a bodily waste isolation device including a pressure differentiation device having an exterior and at least one inner chamber, wherein the pressure differentiation device is capable of maintaining the inner chamber at a pressure lower than an ambient pressure. The bodily waste isolation device preferably also includes at least two resilient elements disposed in the inner chamber of the pressure differentiation device and held under vacuum compression.

31 Claims, 14 Drawing Sheets

DISPOSABLE ARTICLE HAVING BODILY WASTE ISOLATION DEVICE

This application is a continuation-in-part, and claims priority under 35 USC §120 to application Ser. No. 09/107,561 filed Jun. 29, 1998 now U.S. Pat. No. 6,149,636, application Ser. No. 09/106,225 filed Jun. 29, 1998 now U.S. Pat. No. 6,186,991, and Provisional application Ser. No. 60/090,993 filed Jun. 29, 1998.

FIELD OF THE INVENTION

The present invention relates to disposable articles to be fitted to wearers, and more particularly, to disposable articles having a bodily waste isolation device including a compressed vacuum sealed resilient material including a multiplicity of components that is adapted to perform a responsive function upon bodily waste, a wearer, the article or a component or components thereof

BACKGROUND OF THE INVENTION

Today, disposable articles, such as diapers, adult incontinence briefs, sanitary napkins and tampons, are widely used in infant and toddler care and in the care of incontinent adults as a means of containing, isolating and disposing of bodily wastes. These articles have generally replaced reusable, washable cloth garments as the preferred means for these applications because of their convenience and reliability.

While many advancements have been made in the field of disposable articles for both infants and adults, which have enabled them to become widely preferred over conventional cloth garments, a number of problems still exist. Among the problems experienced with these disposable articles are leakage of bodily waste (e.g., urine, feces, menses), skin rash and irritation, contamination of large areas of the wearer's skin with feces, difficult cleanup of bodily wastes such as feces, waste odor, lack of customization to individuals (e.g., fit), etc.

Attempts have been made to address these problems. Super absorbent polymers, for example, have been used to increase the ability of an absorbent article to absorb and retain urine. Barrier leg cuffs have also been used to improve fit and reduce leakage. U.S. Pat. No. 3,860,003, entitled "Contractible Side Portions For Disposable Diaper," issued to Kenneth B. Buell on Jan. 14, 1975, for example, describes an elasticized leg cuff disposable diaper that has achieved wide acceptance and commercial success. Disposable articles have also used pockets, barriers, etc. to contain and prevent leakage of feces from the article. See, for example, U.S. Pat. No. 4,695,278, entitled "Absorbent Article Having Dual Cuffs," issued to Michael I. Lawson on Sep. 22, 1987; U.S. Pat. No. 4,795,454, entitled "Absorbent Article Having Leakage-Resistant Dual Cuffs," issued to Jerry L. Dragoo on Jan. 3, 1989; and U.S. Pat. No. 5,540,671, entitled "Absorbent Article Having A Pocket Cuff With An Apex," issued to Dreier on Jul. 30, 1996. Disposable articles having a selectively expandable or inflatable component that is activated at the point of use or in response to an activating liquid such as water or urine to provide fecal void space or displacement of a topsheet to improve fit have also been disclosed. For example, U.S. Pat. No. 5,330,459, entitled "Disposable Absorbent Article Having an Inflatable Spacer," issued to Gary D. LaVon et al. on Jul. 19, 1994 and U.S. Pat. No. 5,520,674, entitled "Disposable Absorbent Article Having a Sealed Expandable Component," issued to Gary D. Lavon et al. on May 28, 1996 describe disposable absorbent articles having a component that is expandable at the point of use or expands in response to an activating liquid such as water or urine. These expandable components, however, are problematic in that they either require action by the caregiver to activate the components or operate continuously and require too much of a liquid activator to fully expand because the expansion is proportional to the amount of the liquid activator. In addition, self-contracting leg gathers have been disclosed that react with a liquid activator such as water or urine. For example, U.S. Pat. No. 4,246,900, entitled "Diaper Including Moisture-Responsive Seal Means," issued to Friedrich-Wilhelm Schroder on Jan. 27, 1981. Again, these self-contracting gathers have the problem that they either require action by the caregiver to activate the components or operate continuously and require too much of a liquid activator to fully contract because the contraction is proportional to the amount of the liquid activator.

SUMMARY OF THE INVENTION

The present invention is directed to disposable articles such as diapers, incontinent briefs, diaper holders and/or inserts, training pants, feminine hygiene garments, tampons and the like. The disposable article preferably includes a bodily waste isolation device. The bodily waste isolation device preferably includes a pressure differentiation device having an exterior and at least one inner chamber, wherein the pressure differentiation device is capable of maintaining the inner chamber at a pressure lower than an ambient pressure. The bodily waste isolation device preferably also includes at least two resilient elements disposed in the inner chamber of the pressure differentiation device and held under vacuum compression.

BRIEF DESCRIPTION OF THE DRAWINGS

While the specification concludes with claims that particularly point out and distinctly claim the present invention, it is believed that these claims will be better understood from the following description taken in conjunction with the accompanying drawings in which:

FIG. 13 is an enlarged, plan view of an exemplary bodily waste isolation device.

FIG. 13a is a cross-section of the device shown in FIG. 13 taken through section line 13a.

FIG. 14 is an enlarged, plan view of an exemplary bodily waste isolation device.

FIG. 14a is a cross-section of the device shown in FIG. 14 taken through section line 14a.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, article 20, shown in FIG. 1. As used herein, the term "diaper" refers to an absorbent article generally worn by infants and incontinent persons about the lower torso. The present invention is also applicable to other absorbent and non-absorbent articles such as incontinence briefs, incontinence undergarments, absorbent inserts, diaper holders and liners, colostomy type bags for a natural or artificial anus, feminine hygiene garments, tampons, wipes, disposable towels, tissues, water absorbing articles, oil absorbing articles, spill cleanup bags, desiccant bags, disposable mops, bandages and the like.

Figure 1:
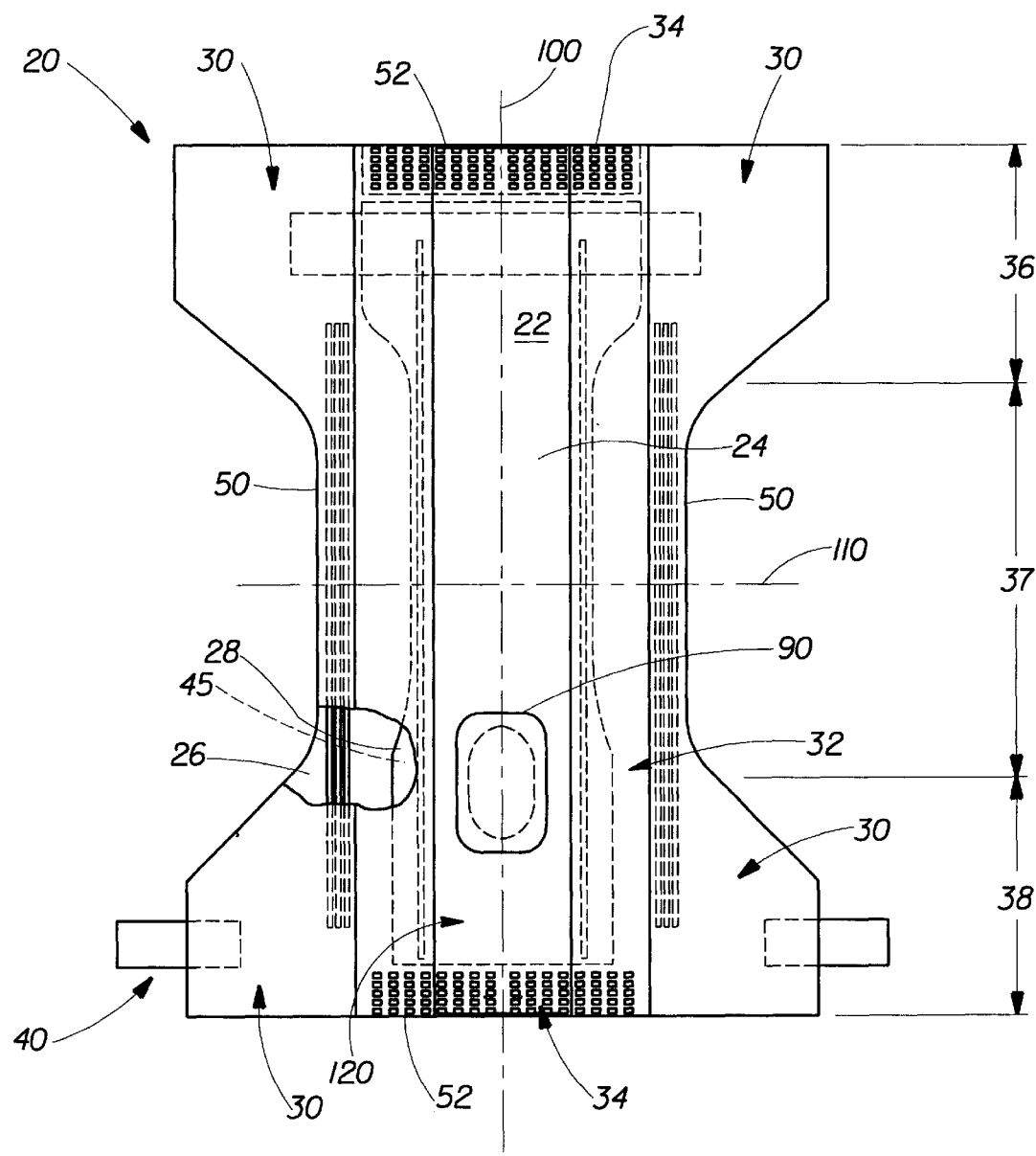
FIG. 1 is a plan view of the article made in accordance with the present invention in a flat-out state with portions of the structure being cut-away to more clearly show the construction of the article, wherein the article is a diaper.

FIG. 1 is a plan view of an article 20 of the present invention, which is shown in this Figure as a diaper, in a flat-out, state with portions of the structure being cut-away to more clearly show the construction of the article 20. The portion of the article 20 which faces the wearer is oriented towards the viewer. As shown in FIG. 1, the article 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 40. Article 20 is shown in FIG. 1 to have a first waist region 36, a second waist region 38 opposed to the first waist region 36 and a crotch region 37 located between the first waist region and the second waist region. The periphery of the article 20 is defined by the outer edges of the article 20 in which the longitudinal edges 50 run generally parallel to the longitudinal centerline 100 of the article 20 and the end edges 52 run between the longitudinal edges 50 generally parallel to the lateral centerline 110 of the article 20.

The chassis 22 of the article 20 comprises the main body of the article 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

The backsheet 26 is generally that portion of the article 20 positioned adjacent the garment facing surface 45 of the absorbent core 28 which prevents the exudates absorbed and contained therein from soiling articles which may contact the article 20, such as bedsheets and undergarments. Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the article 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. Pat. No. 5,865,823 issued to Curro on Feb. 2, 1999. Other breathable backsheets including nonwoven webs and apertured formed films are described in U.S. Pat. No. 5,571,096 issued to Dobrin et al. on Nov. 5, 1996. Each of these references is hereby incorporated by reference herein. In some embodiments such as an insert for article 20, however, the backsheet may be liquid pervious and may, for example, include the same materials as described with respect to topsheet 24 below.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. SELF webs suitable for the present invention are more completely described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The topsheet 24 is preferably positioned adjacent the body surface 47 of the absorbent core 28 and is preferably compliant, soft feeling, and non-irritating to the wearer's skin. Further, at least a portion of the topsheet 24 is liquid pervious, permitting liquids to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the topsheets include fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the name P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 30 are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The lotion may function alone or in combination with another agent as the hydrophobizing treatment described above. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The topsheet 24 and backsheet 26 may be joined to each other, the absorbent core 28 or any other element of the diaper 20 by an attachment means known in the art. For example, the attachment means may include a uniform continuous layer of adhesive, a patterned layer of adhesive, or an array of separate lines, spirals, or spots of adhesive. Alternatively, the attachment means may comprise heat bonds, pressure bonds, ultrasonic bonds, dynamic mechanical bonds, or any other suitable attachment means or combinations of these attachment means as are known in the art.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures).

Exemplary absorbent structures for use as the absorbent core are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The article 20 may also comprise at least one elastic waist feature 34 that helps to provide improved fit and containment. The elastic waist feature 34 preferably extends at least longitudinally outwardly from at least one waist edge 62 of the absorbent core 28 and generally forms at least a portion of the end edge 52 of the article 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the article 20, the elastic waist feature 34 may be constructed as an extension of other elements of the article 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The article 20 may also include a fastening system 40. Some exemplary fastening systems are disclosed in U.S. Pat. No. 3,848,594 entitled "Tape Fastening System for Disposable Diaper" issued to Buell on Nov. 19, 1974; U.S. Pat. No. 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963,140 issued to Robertson et al. on Oct. 16, 1990. Each of these patents is incorporated herein by reference. In alternative embodiments, opposing sides of the garment may be seamed or welded to form a pant. This allows the article to be used as a pull-on type diaper, such as a training pant.

The article 20 may also comprise side panels 30. The side panels 30 may be elastic or extensible to provide a more comfortable and contouring fit by initially is conformably fitting the article 20 to the wearer and sustaining this fit throughout the time of wear well past when the article 20 has been loaded with exudates since the elasticized side panels 30 allow the sides of the article 20 to expand and contract.

While the article 20 of the present invention preferably has the side panels 30 disposed in the second waist region 38, the article 20 may be provided with side panels 30 disposed in the first waist region 36 or in both the first waist region 36 and the second waist region 38. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/915,471 entitled "Absorbent Article With Multi-Directional Extensible Side Panels" filed Aug. 20, 1997 in the names of Robles, et al.; each of which is incorporated herein by reference.

The article 20 preferably further includes leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

Figure 11:
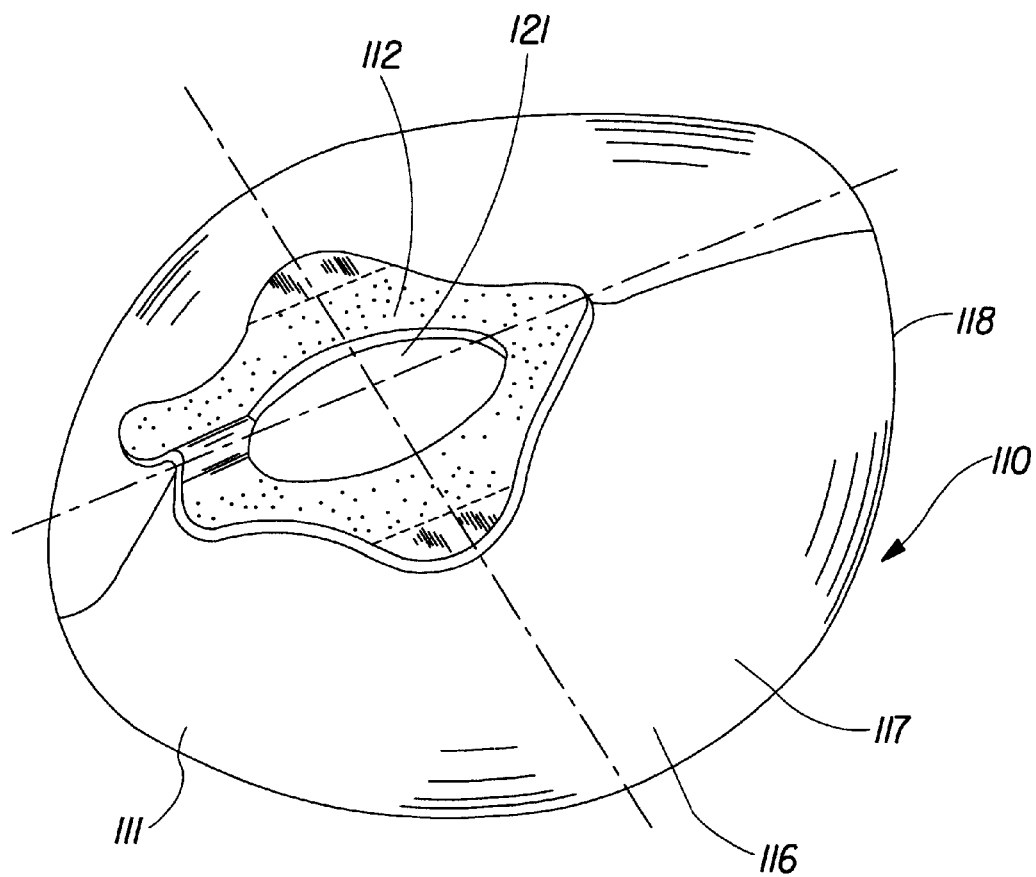
FIG. 11 is a perspective view of a waste bag embodiment of the present invention.
Figure 12:
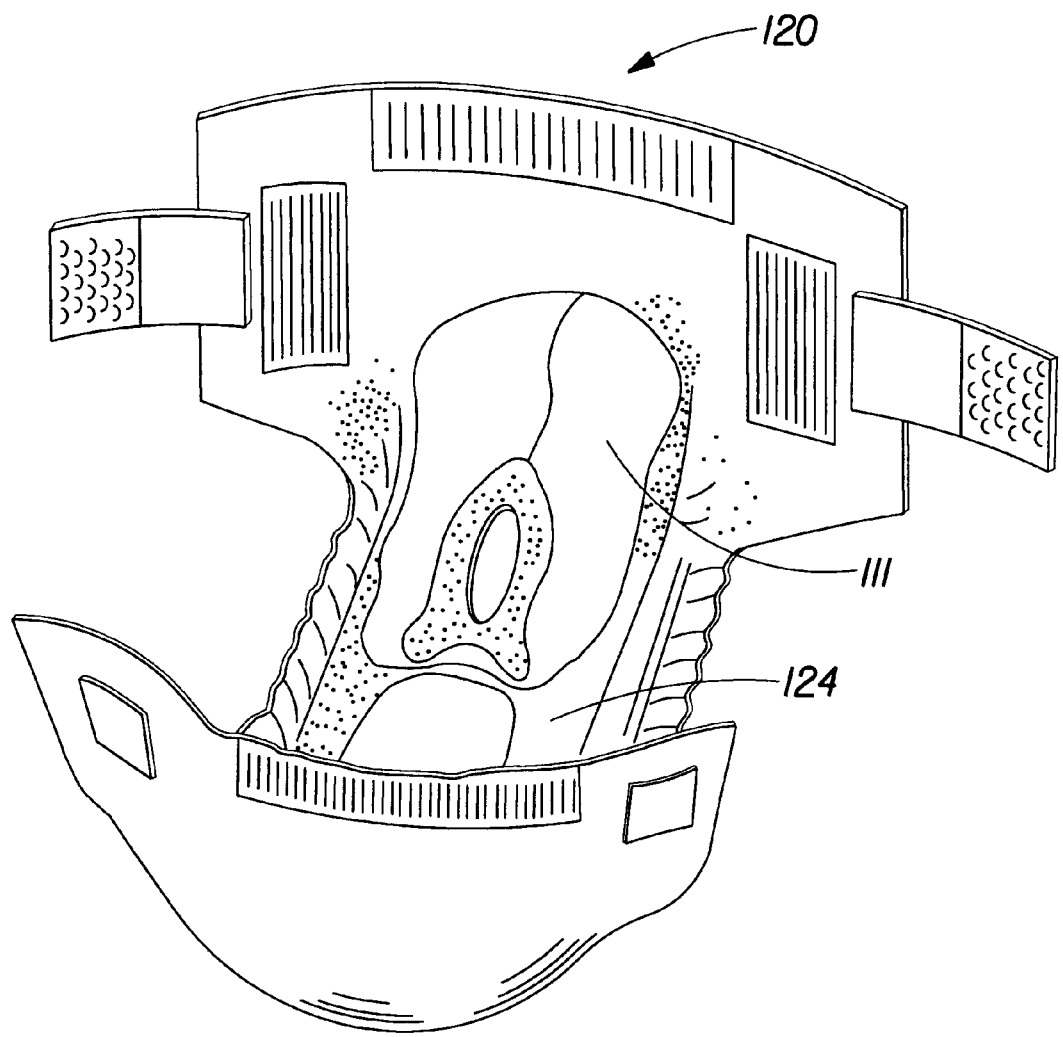
FIG. 12 is a perspective view of an absorbent article including a waste bag.

Embodiments of the present invention may also include a waste management device 110 such as is shown in FIG. 11. The waste management device 110 may include a waste bag 111 to collect feces, urine or both. The waste bag 111 may have an aperture 121 and a flange 112 surrounding the aperture for preferably adhesive attachment to the perianal area of a wearer. Further, the waste management device 110 has been found to be particularly useful and beneficial when used in conjunction with a garment, or diaper, preferably a disposable diaper. One example of a diaper 120 including a waste bag 111 is shown in FIG. 12. If associated with a diaper 120 or other garment, the waste bag 111 may be disposed on or joined to any surface of the article. The bag 111 may be joined to the article by any known means, including any of the joining or attaching means described herein and/or any other joining means such as adhesive, hook and loop fasteners, magnetics, belts, ties, straps, snaps, etc. In one embodiment, the waste bag 111 is joined to the topsheet 124 of the diaper 120.

The waste bag 111 is preferably a flexible receptacle for the containment of excreted fecal matter or urine. Thus, the waste bag 111 is preferably liquid impermeable, and yet it may be breathable. Further, the waste bag 111 is designed of sufficient strength to withstand typical wearing conditions, such as sitting.

The waste bag 111 may comprise one or multiple layers. In one embodiment, the waste bag 111 may comprise three layers, preferably one film and two non-woven layers. The layers of the bag material may comprise any material, preferably so that the bag is liquid impervious. In a preferred embodiment of the present invention a laminate may be formed from a non-woven layer and a film.

Suitable film materials for any of the film layers preferably comprise a thermoplastic material. The thermoplastic material can may be vapor pervious or impervious and can be selected from among all types of hot-melt adhesives, polyolefins especially polyethylene, polypropylene, amorphous polyolefins, and the like; material containing meltable components comprising fibres or polymeric binders including natural fibres such as cellulose - wood pulp, cotton, jute, hemp; synthetic fibres such as fibreglass, rayon, polyester, polyolefin, acrylic, polyamid, aramid, polytetrafluroethylene metal, polyimide; binders such as bicomponent high melt/ low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those described above with respect to the backsheet and monolithic breathable materials such as HYTREL™ available from DuPont and Pebax™ available from ELF Atochem, France.

The waste bag 111 may have any shape or size. Preferred shapes include flat circular type bags, cone shaped bags, truncated cone shaped bags and pyramidal or truncated pyramidal shaped bags and flat T shaped bags. Further, the waste bag 111 may be provided from a unitary piece of material or a number of separate pieces of material which may be identical or different and which may be sealed at their respective peripheries.

The waste bag 111 may also contain absorbent material. The absorbent material may comprise any absorbent material which is capable of absorbing and retaining liquids. The absorbent material may comprise a wide variety of liquid-absorbent materials commonly used in disposable diapers and other absorbent articles. Some examples are described herein with respect to the absorbent core.

The waste bag 111 is provided with an aperture 121 whereby fecal matter or urine is received from the body prior to storage within the bag cavity. The aperture 121 is preferably surrounded by a flange 112 and may be provided in any shape or size, such as circular, oblong, heart shaped and may be symmetrical or asymmetrical, preferably the aperture has an oblong configuration either in the longitudinal or in the transversal direction. The flange may comprise projections designed to fit the perineal, genital and/or coccygeal area of the wearer.

The flange 112 should be made of soft, flexible and malleable material to allow easy placement of the flange 112 to the perianal or uro-genital area. Typical materials include nonwoven materials, wovens, open celled thermoplastic foams, closed-cell thermoplastic foams, composites of open celled foams and stretch nonwoven, and films.

The waste bag 111 preferably further comprises a joining or attachment means to secure the device to the wearer. Such means may comprise any of the joining or attachment means described herein or any other suitable joining or attachment means known in the are such as straps, belts, snaps, ties, hook and loop fasteners, pins, and/or a body-compatible adhesive applied to the wearer facing portion of the waste bag 111 or the flange. Any skin-friendly water resistant pressure sensitive adhesive may be used to attach the device to the perianal or uro-genital area of the wearer, such as hydrocolloid adhesives and hydrogel adhesives. Particularly effective adhesives in providing the desired adhesive properties to secure the flange to the skin of the wearer at the sensitive perianal area, while allowing for relatively painless application and removal, are formed from crosslinking polymers with a plastisicer to form a 3-dimensional matrix.

The article 20 preferably also includes at least one sensor 60. As used in this application, the term "sensor" refers to a device that is used to detect an event or a parameter that is associated with an event. A parameter associated with an event is any measurable signal that correlates with the occurrence of an event within the frame of reference of the system (i.e., a signal caused by the waste, the wearer, or a component thereof). Sensors include anything that responds to one or more specific inputs. Examples of inputs that may be detected by the sensor of the present invention include, but are not limited to, attitude, pressure, motion, moisture, enzymes, bacteria, pH, conductivity, resistance, capacitance, inductance, or other chemical, biochemical, biological, mechanical or electrical properties and/or components of bodily wastes. The sensors preferably detect "non-environmental" inputs such as a non-thermal or a non-relative humidity input in order to minimize the number of false responses by minimizing the possibility of an environmental condition triggering the sensor instead of the sensor detecting an input caused by the waste, the wearer, or a component thereof An electrical or biological sensor may, for example, detect an elimination of bodily waste event such as a defecation, urination or discharge of menses by sensing a component of the waste. A sensor may detect one or more events or one or more parameters associated with an event and provide an input to an actuator or a controller. Further, a sensor of the present invention may also be reversible or irreversible. A dissolving film or capsule is an example of an irreversible sensor, while an electrical sensor that detects electrical activity in muscles of the wearer may receive multiple sequential input signals (i.e., is reversible).

Figure 5:
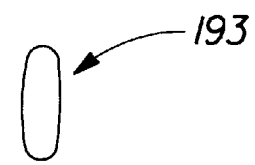
FIG. 5 shows a perspective view of an embodiment of the present invention including a soluble capsule.

As discussed above, sensors 60 of the present invention may include anything that responds to a specific input. For example, the sensor 60 of the present invention may be chemical, biological, mechanical, electrical, etc. A chemical sensor may respond to chemical and/or biochemical inputs such as enzymes typically present in bodily wastes, pH, water, biological inputs such as bacteria, blood or any one or more other components of bodily wastes such as feces, urine, or menses, etc. A chemical sensor may use a chemical reaction as a detection means or may involve a dissolution of a material soluble in an input material of interest. Examples of chemical or biological sensors include dissolving or rupturable films, capsules (e.g. capsule 193 of FIG. 5), cells, seals, etc. that dissolve or rupture in response to a specific chemical, biochemical or biological input or to a specific class of chemical, biochemical or biological inputs. A mechanical sensor may also respond to motion, attitude, pressure, etc. An example of a mechanical sensor is a bellows-type in which when a baby sits on the sensor the weight pushes down on the bellows to inflate a portion of the sensor. A mechanical sensor may also include a sensor or a portion of the sensor that is broken or separated under a pre-defined applied pressure. An electrical sensor may also be used to respond to moisture, urine, feces, menses, pressure, resistance, capacitance, inductance, etc. An electrical sensor may, for example, include a sensor in which a conductive input such as urine or feces completes an electrical circuit; a sensor in which the input such as pressure or tension closes an electrical contact to complete a circuit; a piezoelectric sensor that generates a signal via pressure induced by the wearer or a part of the wearer (e.g., from motion or muscle tone); a sensor in which the resistance, capacitance or inductance varies in the presence of the input to which the sensor responds; or a sensor that receives electrical signals from the body (e.g., from the subcutaneous muscles) of the wearer through a contact such as a skin contact sensor.

In an alternative embodiment, the sensor may be adapted to detect proteins, sugars, bile components, etc. such as described in U.S. Pat. No. 4,636,474 entitled "Toilet Apparatus," issued to Kenji Ogura et al. on Jan. 13, 1987. Further, the sensor may be a biosensor as known in the art (e.g., an enzyme sensor, organella sensor, tissue sensor, microorganism sensor, or electrochemical sensor). Biosensors may comprise bio-recognition systems, typically enzymes or binding proteins such as antibodies immobilized onto the surface of physico-chemical transducers. The biosensors may detect components of bodily wastes, such as ammonia and phenol (e.g., via biosensors comprising enzyme electrodes). A specific strain of bacteria may be detected via biosensors employing antibodies raised against that bacterial strain. Exemplary enzyme electrodes that may be used to detect phenols (e.g. in urine or feces) include tyrosinase based electrodes or polyphenol oxidase enzyme electrodes described in U.S. Pat. No. 5,676,820 entitled "Remote Electrochemical Sensor," issued to Joseph Wang et al. on Oct. 14, 1997 and U.S. Pat. No. 5,091,299 entitled "An Enzyme Electrode For Use In Organic Solvents," issued to Anthony P. F. Turner et al. on Feb. 25, 1992, respectively.

The sensor 60 may be a "proactive sensor" that is capable of detecting changes or signals in or on the body of the wearer, in the article or in the waste, i.e., inputs that directly relate or, at a minimum, correlate to the occurrence of an impending event such as a defecation, urination or other discharge of bodily waste. A proactive sensor, for example, may detect an impending event such as a defecation, urination or discharge or a parameter that correlates to such an event. The impending event may be related to the bodily waste, the wearer, the article, or a component or components thereof A parameter that correlates to an event is any measurable input signal that correlates with the occurrence of the event within the frame of reference of the system (i.e., a signal caused by the waste or the wearer). The proactive sensor may, for example, predict the occurrence of a defecation, urination or discharge of bodily waste or may detect signals that may precede skin rash or irritation.

Proactive sensors in an article may measure many different inputs in order to predict an event. For example, the proactive sensor may monitor the external anal sphincter muscle for a relaxation in the anal sphincter that precedes the release of feces and/or urine, a separation of the buttocks, a pressure change in the abdomen, a gas concentration in the article, or any other indication that may be used to predict or anticipate the occurrence of an event such as a defecation, a urination or a discharge of bodily wastes. Alternatively, a proactive sensor of the present invention may detect signals that precede skin irritation. For example, the sensor may detect residual fecal contamination of the wearer's skin (e.g., fecal enzyme residue left after cleaning up a soiled diaper) that may, over time, lead to irritated skin. Detection of a high pH, an increased skin hydration resulting in a measurable increase in conductance or decrease in impedance of skin, etc. may also be used to predict potential skin irritation. Further embodiments of a proactive sensor are described in copending U.S. application Ser. No. 09/107,561 entitled "Disposable Article Having A Proactive Sensor" (P&G Case No. 7196) filed on Jun. 29, 1998, which is hereby incorporated by reference herein.

The sensor 60 may be disposed in and/or operatively connected to any portion of a disposable article that will be exposed to the input that the sensor is designed to detect. For the purposes of the present invention, the term "operatively connected" refers to a means of communication such that the sensor 60 may signal some portion of the article 20 when the sensor 60 detects an input. The sensor 60 may be separate from and operatively connected to another portion of the sensor 60, another sensor 60, an actuator 70, a controller 80 or some other portion or component of the article 20. "Operatively connected" may, for example, include a means of communication such as an electrical connection via a conductive wire or member, via a transmitted signal such as radio frequency, infrared or another transmitted frequency communication. Alternatively, the sensor 60 may be operatively connected via a mechanical connection such as a pneumatic or a hydraulic connection.

In article 20, for example, the sensor 60 may be located in the front waist region 36, the rear waist region 38 or the crotch region 37 of article 20, and may be integral with, disposed adjacent to, joined to, or comprise a portion of the chassis 22, the topsheet 24, the backsheet 26, the absorbent core 28, side panels 30, leg cuffs 32, a waist feature 34, a fastening system 40, the longitudinal 50 or end 52 edges, etc. The sensor 60 may be integral with the article 20, or may be installed by the caretaker or the wearer. The sensor 60 may be completely contained within the article such as article 20 or may have a receiving portion located in the article such that it will come into contact with the desired input and another portion such as a transmitting portion located either in the article or outside the article. The sensor 60 may be external to the article 20 yet operatively connected to some portion of the article 20 such that the sensor 60 may detect an input external to the article 20 and provide a signal to a controller 80 and/or an actuator 70. In some embodiments, the sensor may be separate from the article, e.g., separately applied to some portion of the wearer, and/or may have one or more component separate from the article.

The sensor 60 may further comprise a sensing "system" including two or more sensors, each of which may detect the same or different signals from the same or different sources. The sensing system may include components that are located inside, external to and/or separate from the article. For example, the sensing system may include a sensor inside the article that detects electrical signals in the external anal sphincter of the wearer and a sensor external to the article that detects motion, tension or muscle activity in the abdomen of the wearer. The sensing system may also or alternatively include components other than the sensing elements inside, external to and/or separate from the article. The sensing system, for example, may include a transmitter that is external to the article and transmits a signal to another part of the sensing system that is joined to or disposed in the article 20.

The article 20 preferably also comprises a mechanical actuator 70. As used in this application, the term "actuator" refers to a device that comprises "potential" and a means of transforming that potential to perform or activate a "responsive function." The potential of the actuator 70 may comprise either stored or potential energy or stored material. The actuator 70 thus may perform or activate a responsive function by transforming potential energy to kinetic energy or by delivering a stored material. A "responsive function" is defined for the purposes of this application as a function performed upon the bodily waste, the wearer, the article, or a component thereof A device that merely provides a signal indicating that an event has occurred, however, is not considered an "actuator" as defined for the purposes of this application. A component of bodily waste may include, for example, moisture, electrolytes, enzymes, volatile gases, bacteria, blood, etc. A component of the wearer may also include skin, genitalia, the anus, the anal sphincter muscle, etc. A component of the article may also include leg cuffs, waist cuffs or other waste barriers and/or containment components, side panels, ears, a chassis, an absorbent core, an acquisition component, a fastening system, the longitudinal or end edges, etc. Potential energy may be stored as mechanical, electrical, chemical or thermal energy. "Kinetic energy" as used in this application refers to the capacity to do work or to perform a responsive function as described above (e.g., expansion of a compressed device, rotation of a twisted device, a gel that moves as it changes phases, coating or treatment of skin or feces, etc.). "Delivery" for the purposes of the present invention refers to a mechanical delivery means such as expanding or moving solid elements, hydraulic effects, gas pressure differentials, valves, etc.

Triggering the creation of a three dimensional structure to capture waste, for example, involves responsive functions performed on a component of the article and, ultimately, on the waste. Capturing waste, wiping the skin of the wearer or treating the skin with a skin care composition, for example, are responsive functions performed on the waste and/or the wearer. Adjusting the article's geometry (in one, two or three dimensions) or physical properties (e.g., bending modulus, geometry, etc.) are examples of responsive functions, which may be performed on the article. Signaling a caretaker and/or the wearer that an event has occurred, however, does not perform a responsive function because it does not perform a function upon the waste, the wearer, the article or a component thereof Signaling devices require an agent external to the system (e.g., a human, etc.) to act as an actuator to result in a function being performed. An actuator of a disposable article may, for example, deliver a deodorant, enzyme inhibitor, skin care composition or pH control agent; capture, wipe, cover, trap, immobilize, seal, pump, or store bodily waste; or trigger the release or creation of a structure or element designed to perform one or more of these functions or any other responsive function upon the waste, wearer, article, or a component thereof.

An actuator 70 of the present invention may release potential energy to perform or activate a responsive function upon the waste, the wearer, the article, or a component thereof. The release of potential energy may transform mechanical, electrical, chemical and/or thermal potential energy into mechanical energy to perform the responsive function. In some preferred embodiments, electrical, chemical or thermal energy may assist or power a mechanical activator. Actuators may be triggered by a threshold level of an input to release potential energy to perform a responsive function or may respond continuously to an input as described below. For example, a compressed foam has stored compressive mechanical potential energy and may provide mechanical kinetic energy when it is released. A twisted foam has stored torsional mechanical potential energy that may provide mechanical kinetic energy, i.e., rotation, when it is released. An actuator of a disposable article, for example, may include one or more of the following: stored lotion, feces modification agents, enzyme inhibitors, pH buffers, dyes, pressurized gas, a compressed foam, a twisted foam, a pump, a closed system liquid transport member, etc. Potential energy may be stored in any manner sufficient to maintain/restrain it until it is required. Examples include batteries and/or capacitors, elastically, torsionally, compressively tensioned materials or structures, in the form of materials capable of performing physical functions (e.g., absorbents, compressed gases, etc.).

Alternatively, an actuator 70 of the present invention may comprise a quantity of a stored material that has the capacity to perform or activate a responsive function upon the waste, the wearer, the article, or any component or components thereof. In one embodiment, for example, the actuator 70 may actively deliver a stored material that performs a responsive function. In this embodiment, the actuator 70 may be triggered by a threshold level of an input to discontinuously deliver the stored material at a given time or may release or deliver the material continuously. The actuator 70 may, for example, include stored lotion, skin care compositions, feces modification agents, enzyme inhibitors, pH buffers, dyes, etc., which are delivered by an actuator 70 such as an expanding resilient material, a released high pressure gas, etc.

In alternative embodiments the sensor and/or actuator may comprise a closed system liquid transport member. A "closed system liquid transport member" or "transport member" comprises a liquid filled member having an inlet port and outlet port, which upon receipt of even a little amount of liquid at the inlet port practically immediately releases liquid at the outlet port. The liquid released from the outlet port may serve as an input signal to a sensor. For example, the liquid may be water, which is released when the transport member imbibes urine at an inlet port, which acts to dissolve a seal to release stored mechanical energy to create a feces void space. Liquid transport through such transport members is based upon direct suction rather than on capillarity. The liquid is transported through a region into which no significant quantity of air (or other gas) may enter. The driving force for liquid flowing through such a member can be created by a liquid sink (e.g., a capillary or osmotic absorbent structure) or source in liquid connection with the member. Thus, a liquid transport member must have a relatively high liquid permeability.

There are preferably at least two regions within the transport member with different pore sizes, namely the one or more port region(s) having smaller pores and the inner region having a much larger pore size. The inner region of transport member has a permeability that is relatively high compared to the permeability of a port region (a higher liquid permeability provides less flow resistance), which can be a part of an outer/wall region circumscribing the inner/ bulk region. Nonlimiting examples of high porosity materials suitable for use as the inner region material include fibrous structures comprising polyolefin, PET, cellulose, and cellulose-based fibers, and porous, open celled foam such as reticulated foams, cellulose sponges, polyurethane foams, and HIPE foams. In one embodiment, the voids of the inner region are essentially completely filled with an essentially incompressible fluid. The term "essentially completely" refers to the situation, where sufficient void volume of the inner region is filled with the liquid such that a continuous flow path between inlet and outlet ports can be established.

The port regions of the transport member comprise materials which are permeable for the transport liquid, but not for the ambient gas (like air) once they are wetted with the transport liquid. Often, such materials are described as membranes, which are defined as regions that are permeable for liquid, gas or a suspension of particles in a liquid or gas. The membrane may for example comprise a microporous region to provide liquid permeability through the capillaries. In an alternative embodiment, the membrane may comprise a monolithic region comprising a block-copolymer through which the liquid is transported via diffusion. Exemplary membranes for the port regions include celluloseacetate membranes, such as also disclosed in U.S. Pat. No. 5,108,383 entitled "Membranes For Absorbent Article" issued to White on Apr. 28, 1992, PET films as disclosed in EP-A-0451797, nitrocellulose membranes, cellulosenitrate membranes, PTFE membranes, polyamide membranes, and polyester. Other suitable materials are woven polymeric meshes, such as polyamide or polyethylene meshes as available from Verseidag in Geldern-Waldbeck, Germany, or SEFAR in Rüschlikon, Switzerland.

The actuator 70 may alternatively comprise an electrically sensitive gel. Electrically sensitive gels are polymeric gel networks that, when at least partially swollen with water, change volume and/or geometry (i.e., perform a mechanical function) under the application of an electric current or field. For example, certain partially ionized polyacrylamide gels will undergo anisotropic contraction of about 50% under weak electric fields (e.g., 0.5 volts/cm) when immersed in acetone and water. Alternative electrically sensitive gels may undergo electrically induced bending in the presence of water and a surfactant or may undergo an oscillating wave motion when subjected to an oscillating electric field. It is believed that local shrinkage may be induced in a portion of the gel, e.g., one side of a gel element, by concentrating positively charged surfactant molecules on the negatively charged gel polymer in an electric field. Changing the intensity and/or the polarity of the field induces a movement in the gel as one side decreases in length (e.g., a gel formed in a strip may curl). Electrically sensitive gels may comprise variable geometries such as rectangular, circular, reticulated grid, etc. patterns in order to provide a valve to release a material, allow a bodily waste to flow through, prevent a bodily waste from flowing through, encapsulate a bodily waste, etc. as they change volume and/or geometry. An exemplary material is a weakly cross-linked PAMPs gel (poly(acrylamido-2-methyl propane) sulphonic acid). This type of gel may perform various functions such as the creation of a void space for feces, wiping the skin, applying or delivering a chemical feces treatment agent, or functioning as a valve to release a material. Other exemplary electrically sensitive gels are described in U.S. Pat. No. 5,100,933 issued to Tanaka on Mar. 31, 1990 and WO 9202005. Alternatively, pH sensitive gels or salt concentration sensitive gels that change volume and/or geometry at specific pH or salt concentrations, respectively, may be used as an actuator of the present invention.

An embodiment of an article of the present invention may include one or more proactive sensors and one or more actuators 70. By detecting an input signal prior to the impending event, a responsive system in the article may be triggered to prepare for the impending event. This will allow the construction of articles in which the waste-management technology is initially "hidden" or unobtrusive, but which is available at, or just before, the moment of need. Regardless of the specific input, the proactive sensor in these embodiments may trigger an actuator to perform an action on the bodily waste, the wearer, the article, or a component or components thereof to prepare for the occurrence of the event. For example, if an impending defecation or urination is to be detected via the electrical activity of the external anal sphincter muscles, the system is preferably triggered (i.e., the responsive system is activated) by a signal related to relaxation of the anal sphincter. The actuator may then perform a function such as treating the wearer's skin to prevent or minimize skin irritation; preparing a bodily waste management device by activating a fecal void spacer; opening a valve to allow urine to flow into a storage device; releasing an enzyme inhibitor, skin care composition, pH control agent, or other skin treatment aids as known in the art.

The actuator 70 may be disposed in and/or operatively connected to any portion of disposable article that will allow the actuator to perform a responsive function upon the bodily waste, the wearer, the article, or a component thereof. In article 20, for example, the actuator 70 may be located in the front waist region 36, the rear waist region 38 or the crotch region 37 of article 20, and may be integral with, disposed adjacent to or joined to a component of the chassis 22, the topsheet 24, the backsheet 26, the absorbent core 28, side panels 30, leg cuffs 32, a waist feature 34, a fastening system 40, the longitudinal 50 or end 52 edges, etc. The actuator 70 may also be completely contained within the article such as article 20, may have a portion located in the article and a portion located outside the article 20, or may be completely external to the article 20. An actuator 70 or a portion of an actuator 70 may be operatively connected to one or more sensors 60, one or more controllers 80, another portion of the actuator 70 or another portion of the article 20. Further, the actuator 70 may be integral with the article 20, or may be installed by the caretaker or the wearer.

The article 20 may also include a controller 80. A "controller" is defined for the purposes of this application as a device that receives an input from a sensor and determines if one or more actions are to be taken. The controller may receive a signal from the sensor 60 and direct the actuator 70 to perform a responsive function upon the bodily waste, the wearer, the article or a component thereof. Alternatively, the actuator 70 may receive the signal directly from the sensor 60 and perform a responsive function upon the wearer, the waste, the article or a component thereof A controller may include materials that undergo chemical or physical change, may be a chemical, mechanical or electrical device that processes information from a sensor, etc. For example, in an article having a resilient compressed plastic foam material encapsulated and held under vacuum compression by pressure differentiation device, such as a moisture soluble bag, the sensor 60 may comprise the moisture soluble bag. As used herein, the term "vacuum compression" refers to a state in which a material is held in an at least partially compressed configuration by means of a structure which maintains a pressure within the structure lower than ambient pressure. In preferred embodiments, the pressure within the structure is no more than about 50% off the ambient pressure. The term "ambient pressure" refers to the atmospheric pressure immediately surrounding the article.

The physical and chemical characteristics of the film, (i.e., the type of polymer, the thickness, etc., that determine how much of the input must be present before the film will dissolve) act as the controller 80 and determine the threshold level of input that must be met before the controller 80 allows the actuator 70 to release stored energy to perform a responsive function. The actuator 70 is the combination of the compressed foam and the loss of vacuum, which allows release of the stored mechanical energy of the compressed foam. In this example, the controller 80 acts as a one-time switch. An electrical controller 80 that receives signals from the sensor 60 such as electrical activity of muscles of the wearer, however, may receive and monitor multiple electrical signals and may repeatedly trigger the actuator. The controller may be integral with the sensor component, integral with the actuator component, or a separate component of the system.

The controller 80 may be disposed in and/or operatively connected to any portion of a disposable article that will allow the controller 80 to receive a signal from the sensor 60 and to provide a signal to the actuator 70. In article 20, for example, the controller 80 may be located in the front waist region 36, the rear waist region 38 or the crotch region 37 of article 20, and may be integral with, disposed adjacent to or joined to the chassis 22, or a component of the topsheet 24, the backsheet 26, the absorbent core 28, side panels 30, leg cuffs 32, a waist feature 34, a fastening system 40, the longitudinal 50 or end 52 edges, etc. The controller 80 may be integral with the article 20, or may be installed by the caretaker or the wearer. The controller 80 may be completely contained within the article such as article 20, may have a portion located in the article and a portion located outside the article, or may be located completely outside the article 20. A controller 80 or a portion of a controller 80 may be operatively connected to one or more sensors 60, one or more actuators 70, another portion of the controller 80 or another portion of the article 20. The controller 80, for example, may receive a signal from the sensor 60 and provide a signal to the actuator 70, e.g., by a radio frequency (rf) transmission.

Although distinct structural elements may perform the sensor 60, actuator 70 and controller 80 functions, the sensor 60, actuator 70 and/or controller 80 functions of the present invention need not be performed by distinct structural elements. The sensor 60 and controller 80 functions, for example, may be performed by the same structural element such as a film that dissolves in contact with a component of a bodily waste. In this example, the film acts as a sensor and responds to the input component of bodily waste. The physical and chemical characteristics of the film, i.e., the type of polymer, the thickness, etc., that determine how much of the input must be present before the film will dissolve act as the controller and determine the threshold level of input that must be met before the controller allows the actuator to release stored energy or deliver stored material to perform a responsive function. In another embodiment, the responsive system may comprise cells or capsules that contain one or more materials such as skin care compositions, pH control agents or enzyme inhibitors. The cells or capsules may, for example, burst under a threshold pressure level and deliver the stored skin care composition or enzyme inhibitor. In this embodiment, the cells or the capsules act as both the sensor, e.g., detecting the pressure level, and the controller, e.g., defining the threshold pressure level before delivering the stored skin care composition or enzyme inhibitors. In yet another embodiment, the responsive system may comprise a closed system liquid transport member that may receive an input such as urine at the inlet port and discontinuously deliver an agent such as a skin care composition, a pH control agent or an enzyme inhibitor at the outlet port of the transport member. In this embodiment, the transport member both acts as the sensor, i.e., receiving urine, and the actuator, i.e., actively delivering the agent to the waste, the wearer, the article or a component thereof to be treated. In addition, the closed system liquid transport member may further act as a controller that determines the necessary threshold level of the input. In an embodiment in which the closed system liquid transport member receives urine at the inlet port and liquid such as water exits from the outlet port to dissolve a soluble film holding a compressed resilient material, for example, the closed system liquid transport member may act as both the sensor and the controller. In this embodiment, the transport member acts as a sensor by receiving the urine and the permeability of the inlet port or the outlet port may function as the controller and determine the threshold quantity of liquid that is required before the transport member delivers liquid to the soluble film.

The article 20 may include a discontinuous responsive system with or without a feedback control loop. The article 20 may alternatively include a continuous responsive system having a feedback control loop. A "responsive system" is defined for the purposes of this application as a system that includes a sensor 60 and an actuator 70 that acts upon the bodily waste, the wearer, the article, or a component thereof when the sensor 60 detects the appropriate triggering input. Upon sensing a given input parameter, the actuator 70 delivers a stored energy or material to perform a responsive function, i.e., acting upon the bodily waste, the wearer, the article, or a component thereof.

The responsive system of the present invention may respond in either a "continuous" or a "discontinuous" manner. As used in this application, a "continuous responsive system" refers to a responsive system in which the output is quantitatively dependent upon the quantity of the input, i.e., continuously increasing quantities of the input are required to effect continuously increasing quantities of the output, or where the output of the responsive system comprises a passive release of a stored material. A super absorbent polymer placed in an absorbent core of an article, for example, provides a continuous response in which the output is quantitatively dependent upon the quantity of the input, i.e., as increasing quantities of liquid waste contact the super absorbent polymer, an increasing amount of the polymer contains that liquid until the capacity of the polymer is exhausted. Another example of a continuous responsive system includes an article that improves the fit of the wearer by releasing a leg cuff that has been held in an expanded state when a film is dissolved in a stoichiometric chemical reaction as it contacts a liquid such as urine or menses and is described in U.S. Pat. No. 4,246,900 entitled "Diaper Including Moisture-responsive Seal Means," issued to Schröder et al. on Jan. 27, 1981. A responsive system that passively releases a stored material, however, generally provides a continuous response regardless of how the material itself is released because the actual responsive function performed upon the bodily waste, the wearer, the article, or a component thereof is performed by the material, not by the release of the material. Thus, whether the material is released continuously in response to a given input, or released discontinuously at a single time when a threshold of a given input is detected, the responsive function performed by the released material is performed such that continuously increasing quantities of the input are required to effect continuously increasing quantities of the output until the material released is exhausted.

Figure 7A:
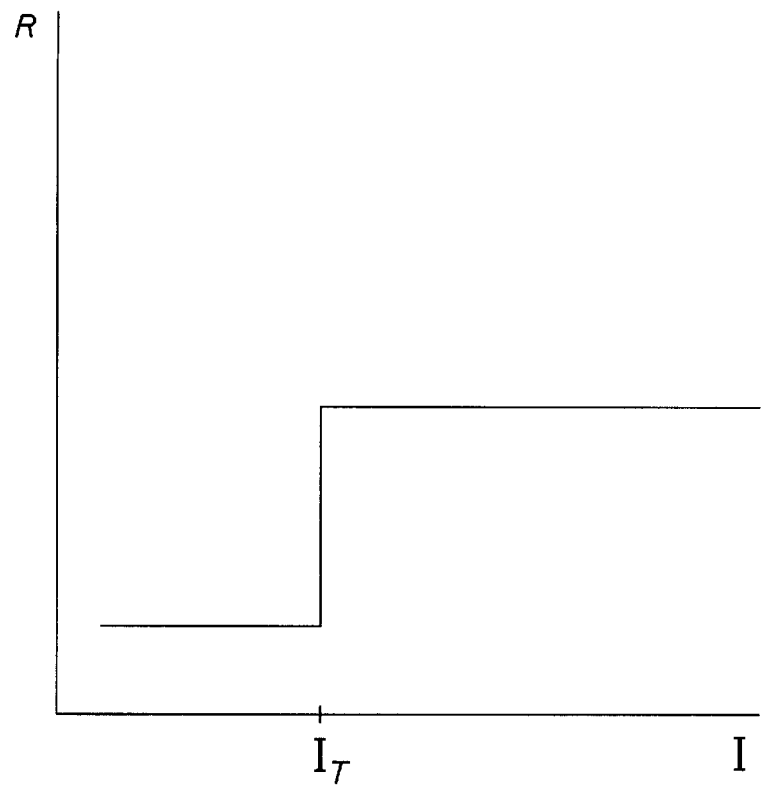
FIG. 7A shows an ideal output function of a discontinuous responsive system of the present invention having a single threshold level.

A "discontinuous responsive system," however, refers to a responsive system that has an output function that is essentially independent of the quantity of the input beyond a threshold level. For example, when one or more threshold levels of a given input are met, the responsive system may release all or a pre-designated portion of its stored energy to perform a specific responsive function. In an ideal embodiment of the present invention, the output function includes a "step" function as shown in FIG. 7A. In this embodiment, the rate of change in the output with increasing levels of input (d(output)/d(input)), i.e., the slope or first derivative f'(x) of the output function f(x), is preferably essentially zero when the amount of input is above or below the threshold level. At the threshold level, however, the d(output)/d(input) rate of change preferably approaches infinity. Thus, in the ideal discontinuous response, the limit of the function f(x−ϵ) as ϵ→0 is not equal to the limit of the function f(x+ϵ) as ϵ→0, i.e., lim f(x−ϵ)≠lim f(x+ϵ).

$$\epsilon \to 0 \quad \epsilon \to 0$$

Figure 8A:
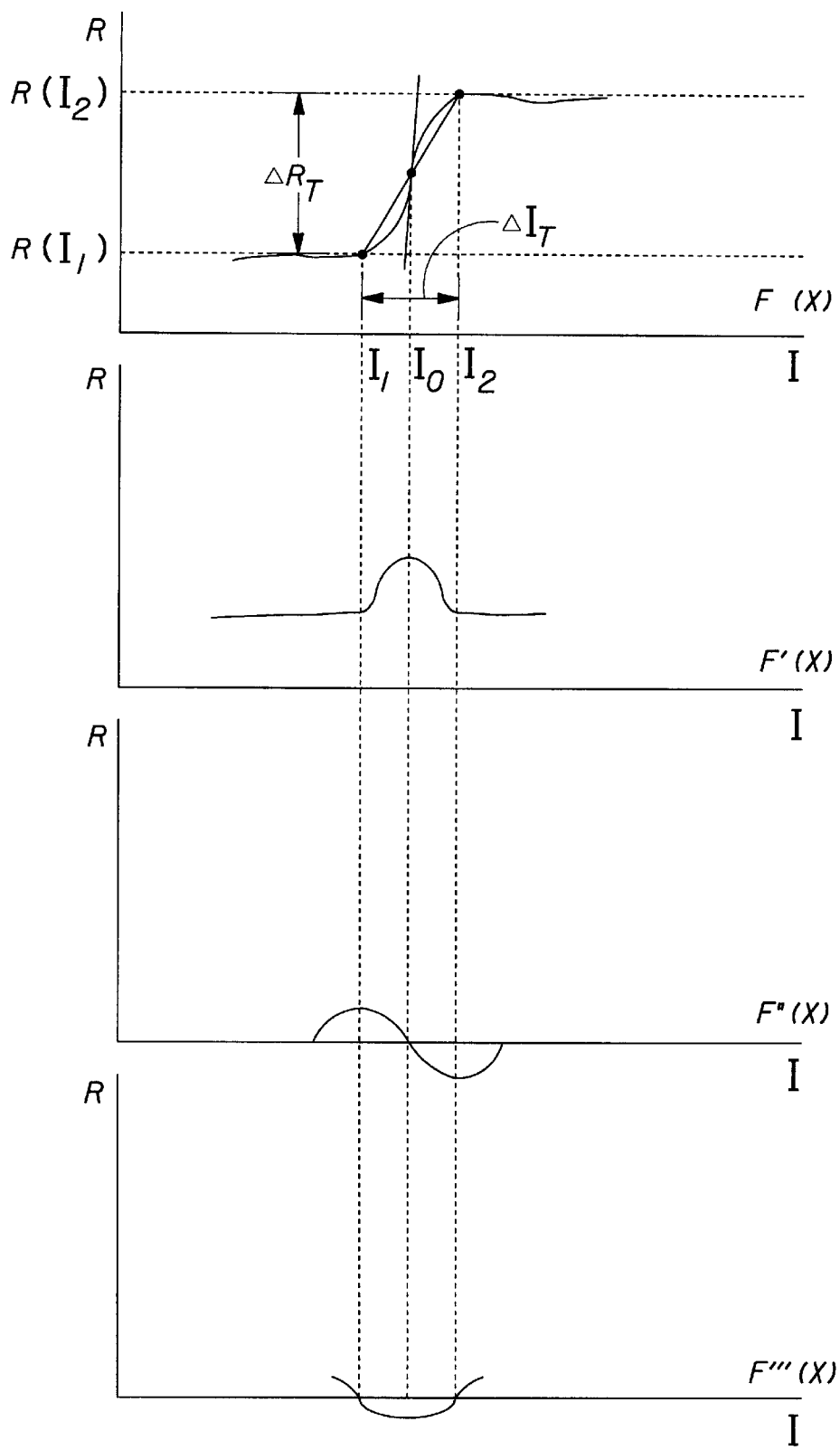
FIG. 8A shows an exemplary output function of a discontinuous responsive system of the present invention along with the first, second and third derivatives of the output function.

The present invention, however, recognizes that in the physical world an ideal instantaneous step change at the threshold level is not necessary and may not even be possible in many instances. In a preferred embodiment, it is only necessary that the output function have a virtual step change with very little change in the input at or around the threshold level of the input. Thus, the present invention contemplates a discontinuous responsive system of the present invention having an output function that responds in a sufficiently discontinuous manner in the transition region such that the output function has at least a minimum relative degree of steepness in the transition region. While not wishing to be limited to a particular method of describing or modeling a discontinuous system, in a preferred method of determining whether a given output function performs in a sufficiently discontinuous manner as defined for the purposes of the present invention, the slope of the output curve at the inflection point is compared with the relative slope of a line between the first and last points of the transition region. For example, FIG. 8A shows a graph of an exemplary output function, f(x) along with aligned graphs of the first, f'(x), and second, f"(x), and third, f'"(x), derivatives of the exemplary output function. The output function f(x) describes the effect of the input (x or I) on the output or response (R(I)). For purposes of the present invention, the transition region is defined as the region between the relative maxima, R(I$_1$), and the minima, R(I$_2$), of the second derivative, f"(x), of the output function, f(x). The relative maxima, R(I$_1$), and the relative minima, R(I$_2$), are points at which the third derivative, f'"(x), equals zero. The inflection point, I$_0$, is defined as the point in the transition region at which the second derivative, f"(x), equals zero, i.e., $$\left. \frac{d^2 R}{d I^2} \right|_{I=I_0} = 0.$$

The comparison of the slope of the output function at the inflection point to the slope of a line between the first and the last points of the transition region can be described by the equation:

$$\left.\frac{dR}{dI}\right|_{I=I_0} = k\frac{(\Delta R_T)}{(\Delta I_T)}.$$

In this equation dR/dI at the inflection point is the first derivative of the output function at that point. The term $\Delta I_T$ is the change in the input to the responsive system between the first, $I_1$, and last, $I_2$, points of the transition region, i.e., $I_2-I_1$, and the term $\Delta R_T$ is the change in the response of the output function between the first and last points of the transition region, i.e., $R(I_2)-R(I_1)$. The coefficient k is a proportional constant that describes the relative steepness of the slope of the output function at the inflection point, $I_0$, compared to the slope of a line between the first and last points of the transition region. In order that the responsive system have a discontinuous output function, the proportional constant k must be at least about 2.0, preferably at least about 3.0, more preferably at least about 5.0, even more preferably at least about 10.0, with at least about 100 being the most preferred.

Figure 8B:
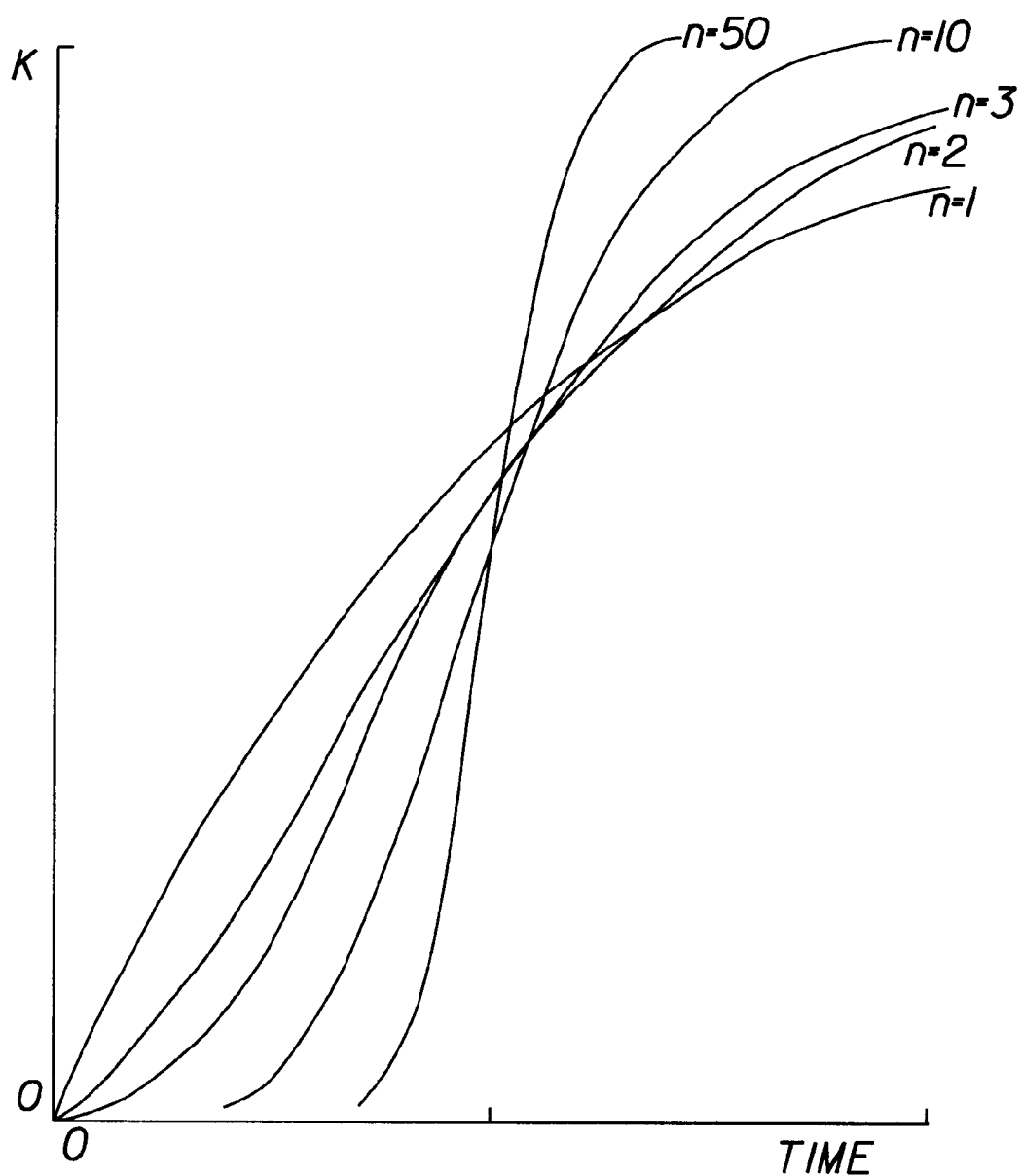
FIG. 8B shows a transfer function of a control system having a series of first order lags having an equal time constant.

In certain embodiments, the relative degree of steepness in the transition region of a discontinuous responsive system may also be modeled by a transfer function of a control system having a series of an integer number, n, first order lags with an equal time constant. The transfer function of the responsive system is defined for the purposes of the present invention as the ratio of the Laplace transforms of the output (responding variable) to the input (disturbing variable). See, e.g., Robert H. Perry & Don Green, *Perry's Chemical Engineers' Handbook,* Sixth Ed., Chap. 22 (McGraw Hill, Inc. 1984). As shown in FIG. 8B, the relative degree of steepness of an output function may be approximated by the formula: $KG(s)=K/(Ts+1)^n$ in which KG(s) is the transfer function, K is a proportional element, T is the time constant of the system, and n is the integer number of first order time lags. In this model, as the number n increases, the steepness of the output function in the transition region increases, and the model begins to approximate a discontinuous responsive system. Certain discontinuous responsive systems of the present invention preferably may be modeled by the above formula when n is greater than or equal to about 25, with n being greater than or equal to about 50 being more preferred, and n being greater than or equal to about 100 being the most preferred.

As shown in FIG. 7A, a responsive system of the present invention may include a single threshold level at which the responsive system may release all of its stored energy to perform a specific responsive function or may include multiple threshold levels at which the system may release a pre-designated portion of its stored energy to perform one or more specific responsive functions at each of the threshold levels. In an embodiment having a single threshold level, for example, the responsive system may release all of its stored energy to perform the entire responsive function when that threshold level is met. In such a single threshold embodiment, In this example, the discontinuous responsive system includes a system that has two states such as on or off When a threshold quantity of an input such as bodily waste is present in the absorbent article, the responsive system may perform a single responsive function upon the waste, the wearer, the article or a component thereof, such as enveloping the waste away from the skin of the user. Thus, the discontinuous responsive system may perform a one-time "switch-like" function that changes from one state to another in the presence of a threshold level of an input.

Figure 7B:
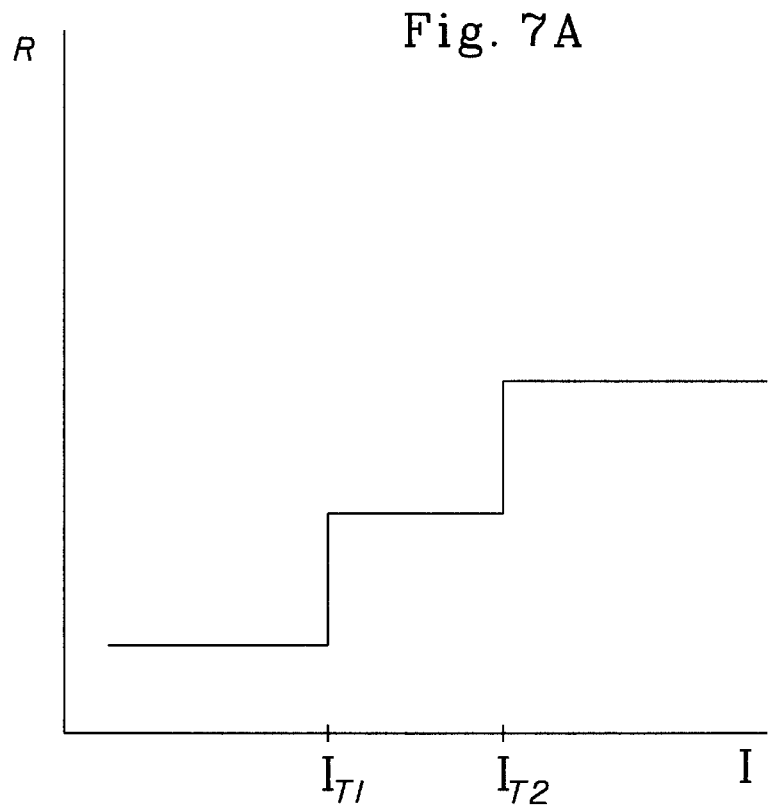
FIG. 7B shows an ideal output function of a discontinuous responsive system of the present invention having multiple threshold levels.

Alternatively, as shown in FIG. 7B, the responsive system may have multiple threshold levels at which when each threshold level is met the system may release a given "quanta" of energy or deliver a given quantity of material to perform a specific responsive function. In this embodiment, when each threshold level is met, a portion of the entire responsive function may be performed and/or different independent responsive functions may be performed in response to different threshold levels being met. For example, a responsive system may monitor a fecal enzyme and when each threshold enzyme level is met may deliver an equal or unequal quantity of enzyme inhibitor(s), or may inflate or expand a storage component of the article or deliver a pH buffer at the first threshold level and perform another responsive function such as delivering a quantity of enzyme inhibitor(s) at the second threshold level. In each transition region, the responsive system responds essentially the same as the transition region in the single threshold embodiment described above.

In addition, a responsive system may monitor multiple inputs such as moisture and/or one or more fecal enzymes and perform one or more responsive functions when the threshold levels of the different inputs are met or may perform one responsive function only when two or more of the threshold levels of the different inputs are met. Thus, a controller may monitor multiple different inputs and perform a different responsive function when the threshold level of the different inputs are met. Alternatively, the controller may perform a logic OR-gate type function such that a responsive function may be performed when one or more threshold levels of the multiple inputs are met. The controller may also perform a logic AND-gate type function such that a responsive function may be performed when each threshold level of two or more different inputs is met.

The responsive system may also comprise a "closed loop" or an "open loop" system. A "closed loop" system, which is also referred to as a "feedback control loop" system, includes distinct sensor 60 and actuator 70 components and uses a detection or a measurement of an element or a parameter of the output condition as at least one trigger of a responsive function that is performed upon the input. The output condition may be the state of the input condition after the actuator 70 has had the opportunity to perform a responsive function on the input condition. For example, if the sensor 60 is monitoring pH in the article 20 and urine is discharged into the article 20 changing the pH of the system, i.e., the output condition of the responsive system, the responsive system may deliver a predetermined quantity of a pH buffer to bring the pH of the system back to the desired target pH or pH range or may release a buffer until the pH returns to the target pH or the pH range. An absorbent material such as a super absorbent polymer that continually absorbs a liquid input until the liquid has all been absorbed or the capacity of the polymer has been reached, however, is not considered to comprise a closed loop system because the absorbent material does not have distinct sensor 60 and actuator 70 components. The responsive function may be performed when the output condition reaches a threshold level, or may be performed only when the output condition and one or more other conditions are met. Acting upon the input may include acting upon the element sensed, e.g., sensing pH and acting upon the pH, or may include acting upon a composition of which the element sensed is an integral component, e.g., sensing a fecal enzyme or fecal moisture and acting upon feces. As described above, a feedback control loop system includes at least two distinct components: the sensor 60 and the actuator 70. The sensor 60 detects an event, or a parameter associated with that event. The actuator 70 receives a signal and performs a responsive function on the input condition detected by the sensor 60. The feedback control loop may further include a controller 80. In this case, the sensor 60 provides a signal to the controller 80, and the controller 80 directs the actuator 70 to perform a responsive function upon the input condition. The controller 80 may be a separate component of the responsive system or the controller function may be performed by the sensor 60 and/or the actuator 70.

The feedback control loop may be "non-modulating" or "modulating." In a "non-modulating" feedback control loop responsive system the responsive system acts as a one-time switch in which the actuator performs a responsive function on the input when the threshold level of the output condition is met. For example, the sensor 60 may detect a specific fecal enzyme, and the actuator 70 may release a compressed foam in response to capture the feces or may deliver an enzyme inhibitor in response that acts upon the enzyme detected in the feces. Alternatively, the sensor 60 may detect urine or menses moisture and release a compressed foam or absorbent material in response that draws the moisture into the material as it expands. The sensor 60 may also detect a volatile gas that produces an offensive odor, and the actuator 70 may release a deodorant in response that eliminates the odor of that volatile gas. In each of these examples, the actuator 70 acts upon the input detected by the sensor 60. If the sensor 60 detects urine and the actuator 70 releases a compressed foam material to create a shaped void of sufficient volume to contain feces, however, the actuator 70 acts upon something other than the input detected by the sensor 60, i.e., acts upon the feces instead of the urine and is therefore not a feedback control loop. A "modulating" feedback control loop, however, includes a sensor 60, an actuator 70 and a controller 80. In a modulating feedback control loop, the output condition is monitored constantly or repeatedly, and the controller 80 directs the actuator to perform a responsive function on the input in order to maintain the output condition at a desired set point or within a desired range. A modulating responsive system may constantly or repeatedly measure pH in waste and deliver a given quantity of a pH control agent (such as a pH buffer or a pH decreasing agent) each time the pH of the waste is detected above a threshold pH level to provide a feedback control loop responsive system.

An "open loop" system, however, is a system that responds to the input to perform a responsive function without using feedback, i.e., the output has no effect upon the sensed input entering the system. An open loop system may include a responsive system that has a single device that performs the functions of both the sensor 60 and the actuator 70 or may have distinct sensor 60 and actuator 70 components in which the actuator acts upon something other than the input. A super absorbent polymer placed in an absorbent core of a disposable absorbent article, for example, provides an open loop response because the polymer only includes a single device that performs the functions of the sensor 60 and actuator 70. Alternatively, an open loop responsive system may include a sensor 60 that detects bodily waste or a component of that bodily waste, and an actuator 70 that performs a responsive function in a continuous or a discontinuous manner on something other than the input detected by the sensor 60. For example, the sensor 60 may detect urine, and the actuator 70 may capture or store feces. One example of a continuous open loop responsive system in which an inflatable spacer inflates to provide a void volume to store feces via a stoichiometric chemical reaction when a liquid such as urine contacts a gas evolving material, i.e., a continuous responsive system, is described in U.S. Pat. No. 5,330,459 entitled "Disposable Absorbent Article Having An Inflatable Spacer," issued to Gary D. Lavon et al. on Jul. 19, 1994, which is incorporated herein by reference. Another example of an embodiment of this type is a disposable article that improves the fit on the wearer by the actuator releasing a leg cuff that has been held in an expanded state when the sensor 60 detects a liquid such as urine or menses. An example of a continuous open loop responsive system that improves the fit of the wearer via a stoichiometric chemical reaction is described in U.S. Pat. No. 4,246,900 entitled "Diaper Including Moisture-responsive Seal Means," issued to Schröder et al. on Jan. 27, 1981, which is incorporated herein by reference. Alternatively, a discontinuous open loop responsive system that improves the fit on the wearer may include an elastic material such as a leg or waist cuff that is held in an expanded state at two distinct restraint points by a soluble restraining material such that when the restraining material at one or both of the restraining points dissolves, the elastic material may contract and form a seal with the skin of the wearer.

Figure 6A:
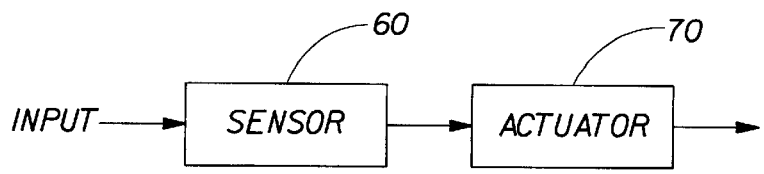
FIG. 6A shows a block diagram of an exemplary open loop responsive system.
Figure 6B:
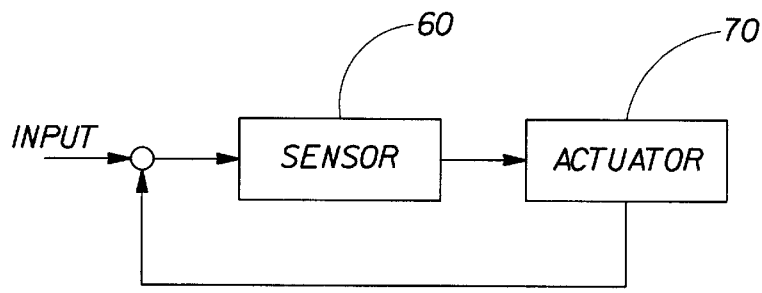
FIG. 6B shows a block diagram of an exemplary closed loop responsive system.
Figure 6C:
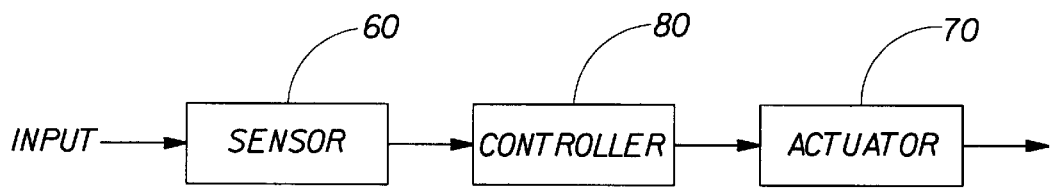
FIG. 6C shows a block diagram of an exemplary open loop responsive system including a controller.
Figure 6D:
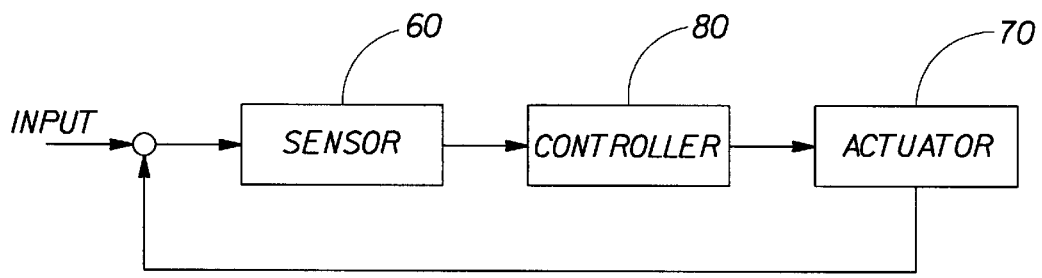
FIG. 6D shows a block diagram of an exemplary closed loop responsive system including a controller.

A block diagram of an exemplary open loop responsive system having a sensor 60 and an actuator 70 is shown in FIG. 6A. A block diagram of an alternative open loop responsive system including a sensor 60, an actuator 70 and a controller 80 is shown in FIG. 6C. A block diagram of an exemplary closed loop responsive system having a sensor 60 and an actuator 70 is shown in FIG. 6B. A block diagram of an alternative closed loop responsive system including a sensor 60, an actuator 70 and a controller 80 is shown in FIG. 6D.

The present invention may include a discontinuous responsive system having a mechanical actuator that includes either an open loop or closed loop. In addition, the present invention may include a continuous responsive system having a mechanical actuator that also comprises a feedback control loop (i.e., a closed loop system). Each of these types of responsive systems provide distinct advantages over the continuous open loop responsive systems known in the art.

One embodiment of the present invention includes a bodily waste isolation device 90 comprising a resilient material 94 that is held in a compressed state by a pressure differentiation device 91. A pressure differentiation device, as used herein, is any device or structure that can maintain a resilient material in a compressed state (e.g., can store energy by providing a constraining pressure on the compressed resilient material 94). A "compressed state" is defined as the condition in which a material is maintained at a smaller volume than the material would have if unconstrained and under zero applied pressure. With respect to resilient materials, a compressed state may generally be achieved by applying a pressure to a surface of the material or via any other means known in the art. The pressure differentiation device may, for example, comprise a vacuum sealed bag or tensioned materials, such as elastic or inelastic bands or strands, strips, films, nonwoven, scrims, or foams, that constrain a resilient material. Preferably, the compression of the resilient material maintained by the pressure differentiation device 91 may be at least partially reduced (i.e., the compressed resilient material 94 may at least partially expand) via a trigger mechanism. A trigger mechanism is any element or device, such as a sensor, actuator, or combination thereof, that responds to an input to effect the equalization of pressure in the pressure differentiation device 91 and allow the compressed resilient material 94 to at least partially expand.

Figure 9A:
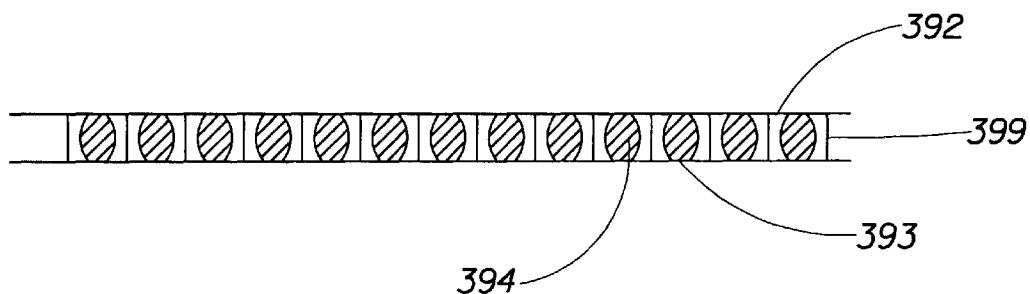
FIGS. 9A–C show a sectional view of an embodiment of a responsive system including a mechanical pump of the present invention.
Figure 9B:
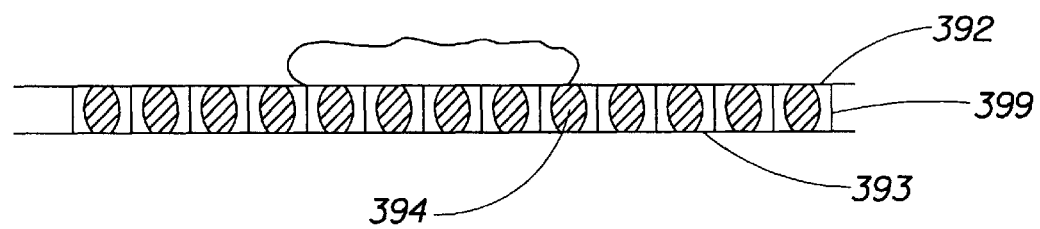
Figure 9C:
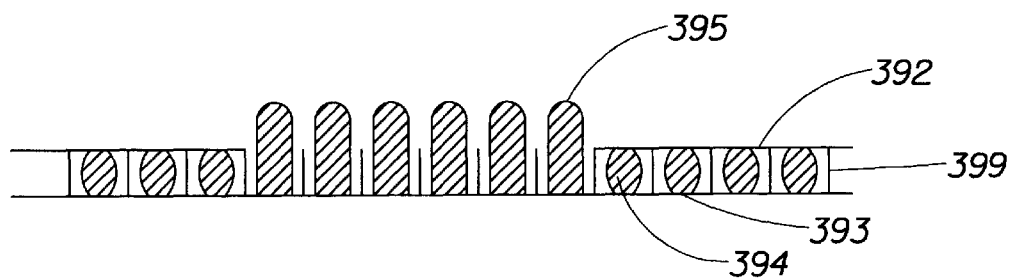
Figure 10:
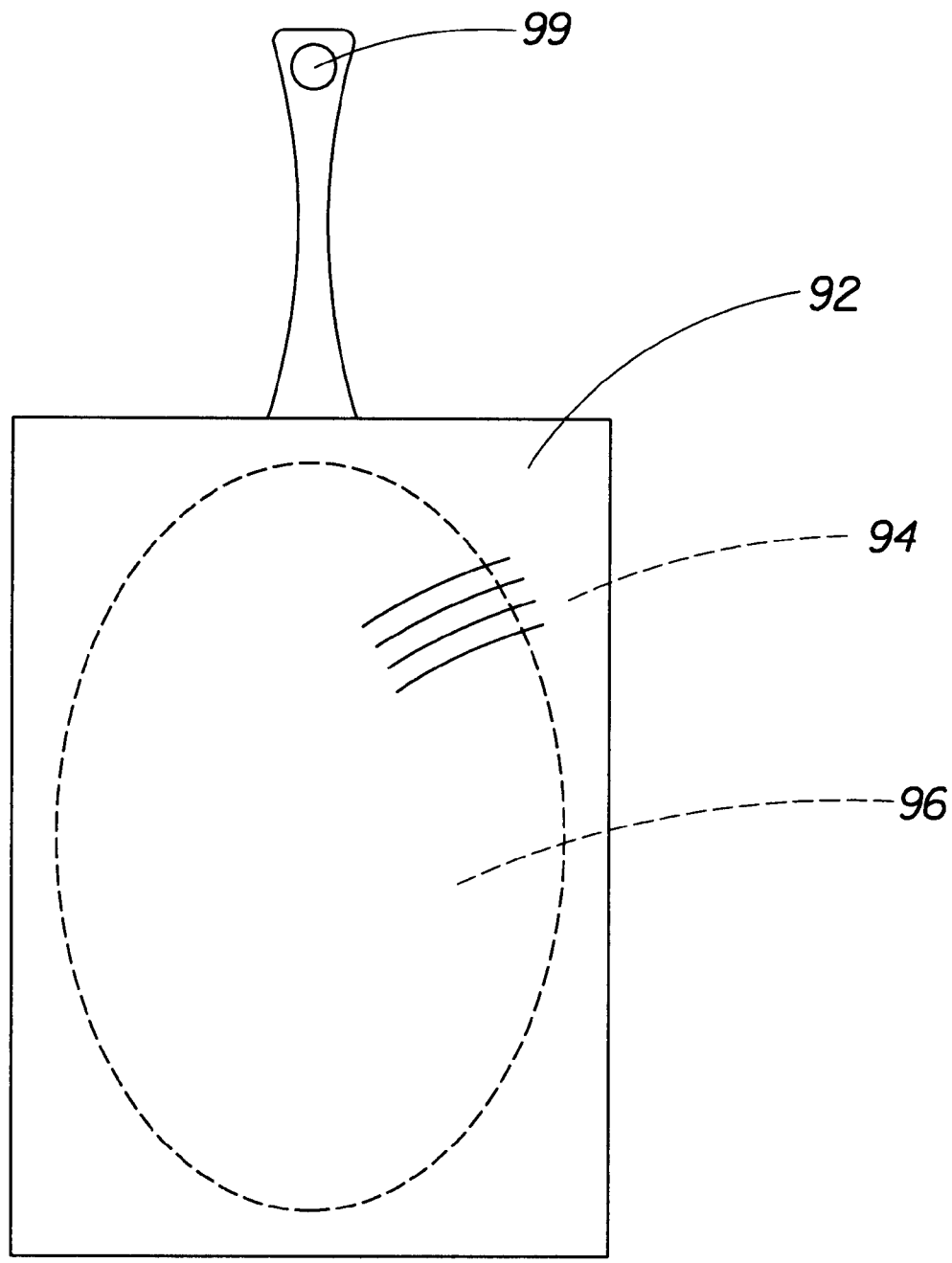
FIG. 10 shows a perspective view of an alternative embodiment of a bodily waste isolation device of the present invention.

The bodily waste isolation device 90 may be placed in the article 20 adjacent to the anus of the wearer so that when it is allowed to expand it may capture bodily wastes such as feces and store the waste away from the skin of the wearer. In this embodiment, if the soluble bag responds to fecal moisture and the bodily waste isolation device captures feces in response to the fecal moisture, the responsive system comprises a discontinuous closed loop responsive system because the system acts upon the sensed input in a discontinuous manner when a threshold level of the input is present. If the soluble bag responds to urine, however, the responsive system comprises a discontinuous open loop system because the responsive system acts upon something other than the input, i.e., the system captures feces instead of urine. An example of such is shown in FIG. 10 in which a soluble seal 99 may be placed in a portion of article 20 where urine is likely to be deposited. Alternatively, the resilient material 94 may be an absorbent material that functions as a pump by drawing fluid into its body as it expands. As shown in FIGS. 9A through 9C, for example, a high porosity, large cell, resilient foam 394 as described above may be compressed and contained in a film, envelope, bag or capsule having at least a soluble portion 392 and an insoluble backing 393. FIG. 9A shows an example of a mechanical pump of the present invention. FIG. 9B shows feces on the structure, and FIG. 9C shows the structure after the feces is absorbed. Preferably, each cell comprising the compressed foam is individually held under vacuum. When a liquid such as urine, menses or fecal moisture contacts the soluble film, the film dissolves and allows the compressed foam in the cells contacted by the feces to expand and draw fluid into the foam as it expands. In one embodiment, the absorbent material may include multiple cells that are individually vacuum sealed via cell walls 399 in order to maintain a suction with overlying waste. In this embodiment, if the responsive system pumps the fluid that is detected by the soluble material, the responsive system comprises a discontinuous closed loop responsive system because the system acts upon the input detected by the sensor.

Figure 2:
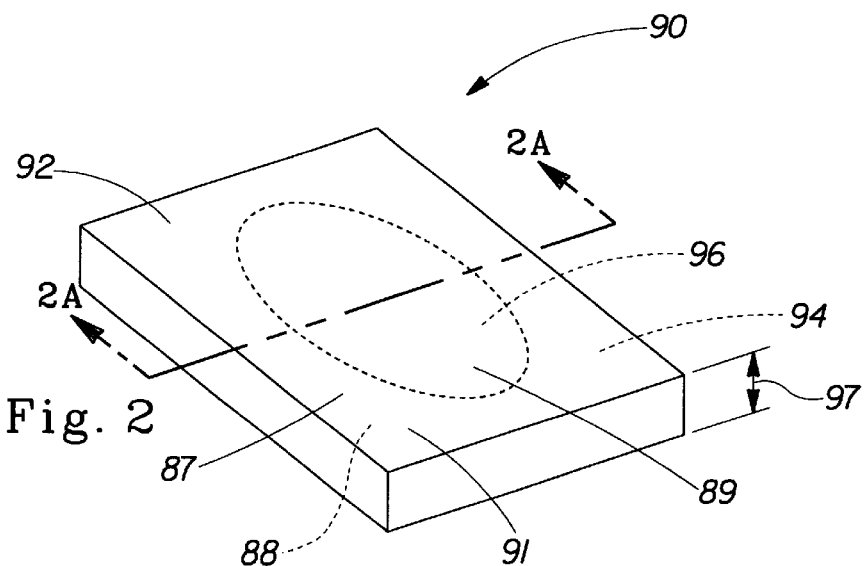
FIG. 2 shows a perspective view of a bodily waste isolation device of the present invention in a compressed state before activation.
Figure 2A:
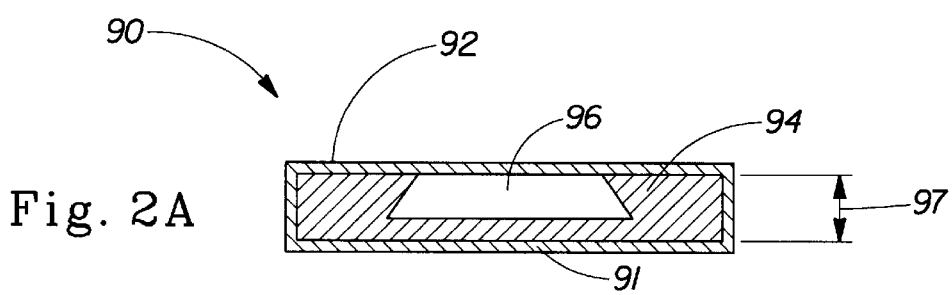
FIG. 2A shows a sectional view taken along line 2A—2A of FIG. 2.
Figure 3:
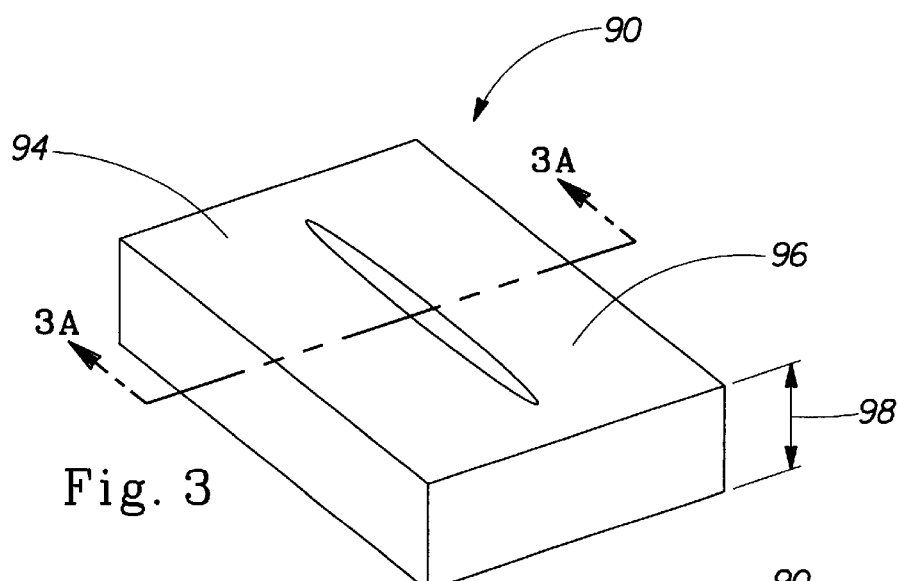
FIG. 3 shows a perspective view of one embodiment of FIG. 2 after activation.
Figure 3A:
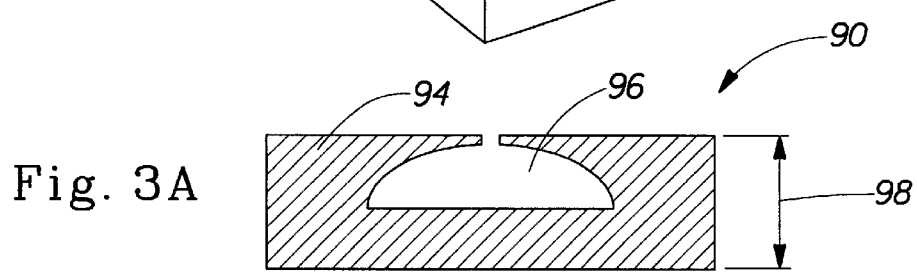
FIG. 3A shows a sectional view of FIG. 3 taken along line 3A—3A of FIG. 3.

In the embodiment of the present invention shown in FIGS. 1–3, the pressure differentiation device 91 comprises a bag 92 which includes an exterior 87 and an inner chamber 88. At least a portion of the bag 92 is preferably water soluble and functions as a trigger mechanism 89. Preferably, the resilient material 94 is held within the inner chamber 88 of the pressure differentiation device 91 under vacuum compression. That is, at least a portion of the resilient material 94 is maintained in an at least partially compressed state by the pressure differentiation device 91. In preferred embodiments, the pressure in the inner chamber 88 is lower than the ambient pressure, thereby providing a means to maintain the resilient material 94 in at least a partially compressed state. In this embodiment, the ambient pressure is the atmospheric pressure. When a threshold level of an input is reached or sensed, the trigger mechanism 89 may effect an increase in the pressure in the inner chamber 88, allowing at least a portion of the compressed resilient material to expand to at least a portion of its uncompressed thickness. For example, when a threshold level of moisture (i.e., the input) dissolves a portion of the water soluble bag 92 or seal and allows the pressure difference between the inner chamber and the ambient pressure to equalize, the resilient material 94 expands.

The resilient material may be any suitable shape when compressed or expanded. For example, the resilient material may be a resilient synthetic polymer or plastic foam that has a shaped void that, when expanded, has a sufficient volume to capture feces. Alternatively, the resilient material 94 may comprise micro- or macroporous foams, loop structures, springs, resilient highloft nonwovens, coiled structures, or various shapes of resilient materials elastically deformed into a lower-volume, constrained geometry. Further, the resilient material 94 may comprise two or more resilient elements comprising the same or different materials. For example, the resilient material 94 may comprise both microporous and macroporous elements such as micro and macroporous foams. In any case, the individual resilient elements of the resilient material may be configured in any suitable manner, including at least partially overlapping, abutting or non-touching or completely separate from each other.

The bodily waste isolation device 90 is shown located in the urine loading zone in FIG. 1.

In the bodily waste isolation device 90 embodiment shown in FIGS. 2 and 3, the resilient material 94 may comprise any elastically deformable foam that has suitable compression and recovery properties so that it is capable of being compressed and held within the pressure differentiation device 91 (e.g., bag 92) and also capable of recovering a substantial proportion of its original height, preferably at least about 75%, after release of a constraining force. At least a portion of the bag 92 may comprise a soluble region or a soluble seal. The soluble seal may be integral with the bag 92 (e.g., a portion of the bag 92 material) or may be a separate element (e.g., a soluble material affixed over a hole or permeable region in the bag 92). The soluble region or seal may dissolve when contacted by water, urine, fecal enzymes, etc. The bag 92 preferably retains the resilient material 94 under vacuum compression until a portion of the soluble region of the bag 92 dissolves enough (i.e., a threshold level of water is detected) to discontinuously release the vacuum, and, thereby, the stored energy in the compressed resilient material 94. Once expanded, the foam is also preferably rigid enough to withstand the weight of a baby, for example, so that the foam will not compress significantly, preferably less than about 50%, and release the captured waste if the baby sits on the device. An EVA foam, for example, such as the ones available from Foamex Corporation of Eddystone, Pennsylvania identified as SIF/210PP1 or Aquazone 80A foam, or from Sentinel Products Corporation of Hyannis, Mass. identified as MC1900 EVA 2 lb/ft$^3$, or a HIPE foam as described in U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997 may be used as the feces capture compression material 94.

Figure 4:
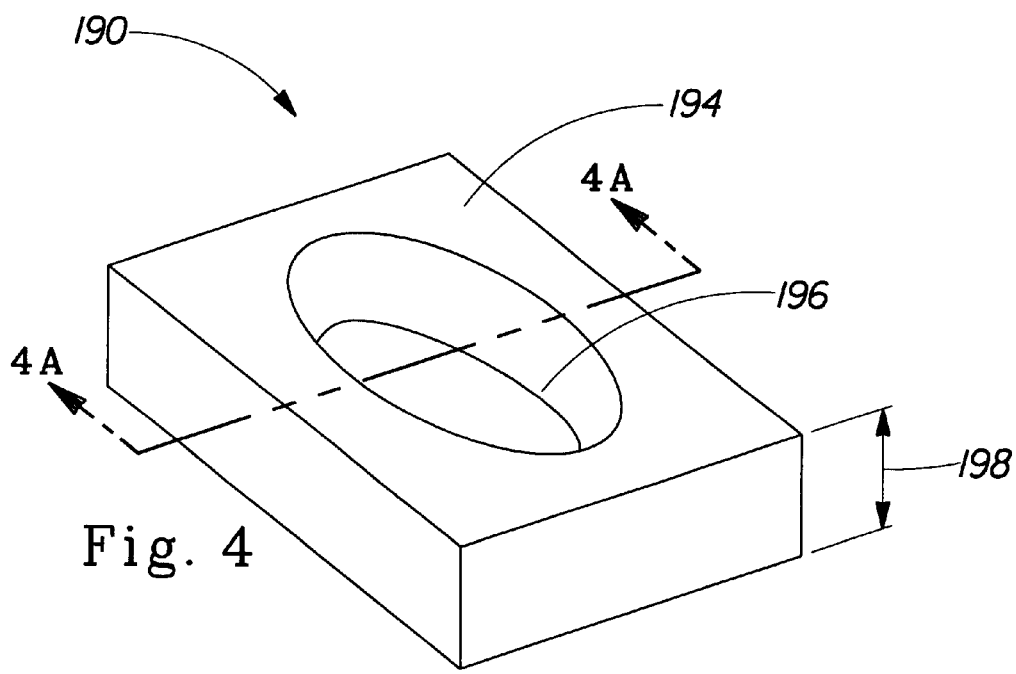
FIG. 4 shows a perspective view of an alternative embodiment of FIG. 2 after activation.
Figure 4A:
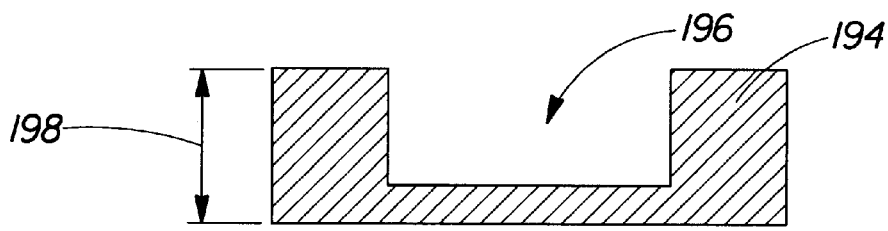
FIG. 4A shows a sectional view of FIG. 4 taken along line 4A—4A of FIG. 4.

As shown in FIG. 2, the compression material 94 may include an aperture 96 that is open when the resilient material 94 is compressed. When the resilient material 94 expands, the aperture 96 may be enclosed by the perimeter of the resilient material 94 as shown in FIG. 3. This allows the waste to be captured or encapsulated away from the skin of the wearer inside the aperture of the resilient material. Alternatively, as shown in FIG. 4, the resilient material 94 may have an open aperture that acts as a spacer and provides a void space having a sufficient volume to store bodily waste deposited in the article 20. This allows the resilient material 94 to receive multiple bodily waste insults after the resilient material 94 has expanded.

As noted above, the resilient material 94 may comprise two or more individual resilient elements comprising the same or different materials. For example, the resilient material may comprise both microporous and macroporous resilient elements such as micro- and macroporous foams. The resilient material 94 may comprise a first resilient element which preferably comprises macroporous reticulated polyurethane foam (e. g., PG14848T20 having 20 pores per square inch from PCF Foam Corporation of Hamilton, Ohio) having an opening 96 for feces storage and an extension into the urine loading zone. The resilient material 94 may additionally comprise a second resilient element (e.g. a microporous foam such as those described in U.S. Pat. Nos. 5,260,345 and 5,625,222 cited above). Preferably, the second resilient element has an opening for feces generally coextensive with the opening 96 in the first resilient element and is disposed on the wearer-facing side of the first resilient element, except in the urine loading zone. (However, embodiments are contemplated wherein the first resilient element is disposed on the wearer facing side of the second resilient element.) The first resilient element may serve to promote air flux to at least a portion of the second resilient element once the soluble bag 92 or seal is dissolved. This preferably results in a rapid expansion of at least the second resilient element as the pressure inside equilibrates with the ambient pressure. Preferably, the larger pores in the first resilient element (e.g. macroporous foam) do not become obstructed by residual partially dissolved bag material, providing a clear air pathway for rapid pressure equalization in the rest of the bag and/or resilient material 94.

The various components of the resilient material may also differ from each other in any property, including compressive modulus, bending modulus, thickness, pore size distribution, chemical composition, porosity, and surface energy. In one nonlimiting example, the first and second resilient elements may compress in the range between about 50% and about 80% and about 5% and about 50%, respectively, under an applied pressure of about 1.0 psi. Preferably, at least one of the components in a multiple component system compresses no more than about 25% under an applied pressure of about 1.0 psi. However, regardless of the construction, the opening 96 in the resilient material preferably provides an available volume of at least about 20 cubic centimeters under an applied pressure of about 0.1 psi once the structure has been activated (e.g., via water dissolving an encapsulating film).

Figures 13, 13A:
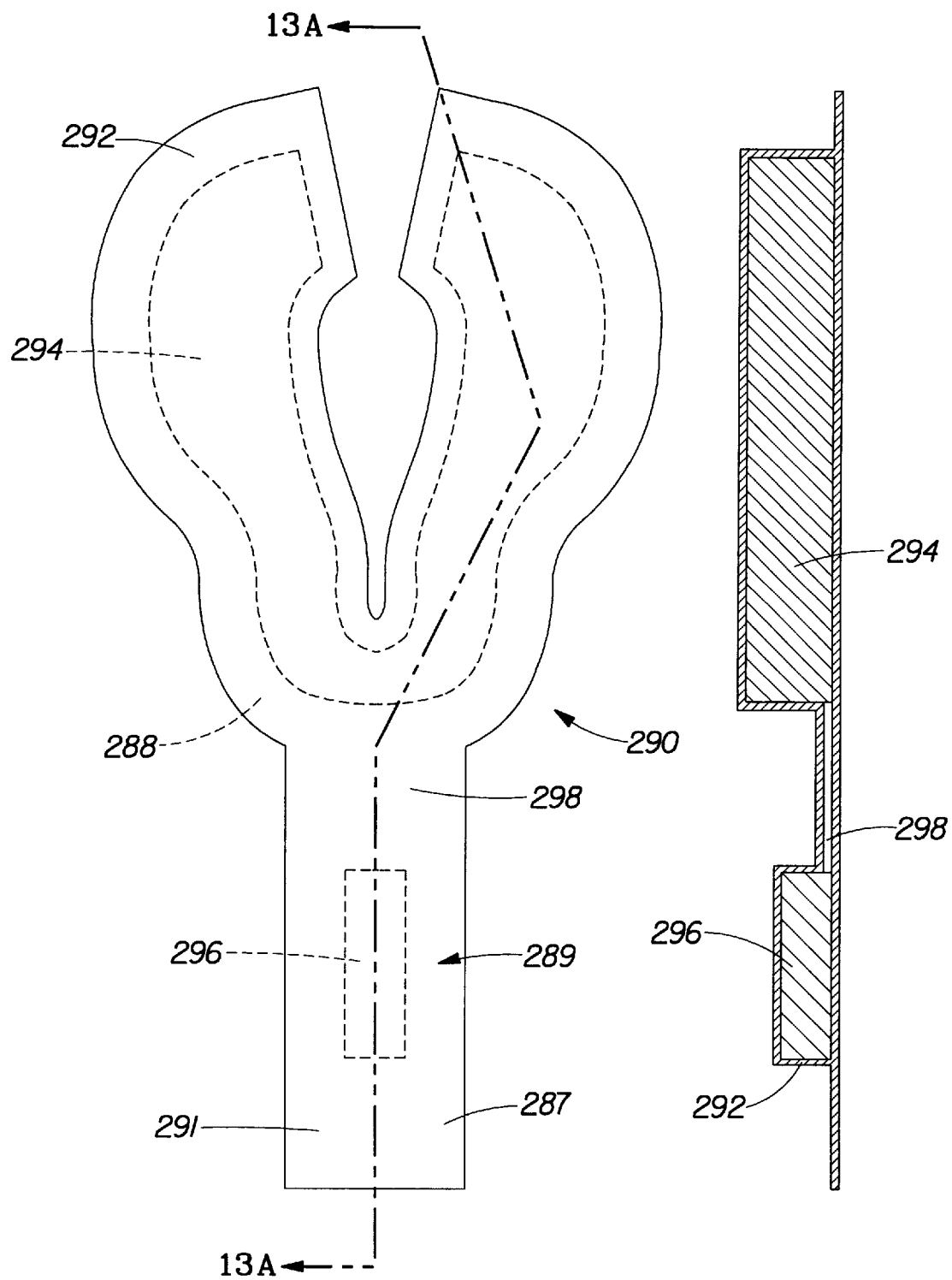

As shown in FIGS. 13 and 13a, the present invention may include a bodily waste isolation device 290 including two or more resilient elements 294 and 296 which are separate from each other and not directly touching or directly joined to each other but at least a portion of each which are both held under vacuum compression. The resilient elements 294 and 296 are preferably held under vacuum compression within a pressure differentiation device 291. The pressure differentiation device 291 preferably includes an exterior and an inner chamber 288. The exterior 287 of the pressure differentiation device 291 preferably keeps the inner chamber 288 at a pressure which is less than the ambient pressure of the atmosphere surrounding the article until a predetermined event takes place, such as urination or defecation. Further, the bodily waste isolation device 290 preferably includes a trigger mechanism 289 which is capable of releasing the pressure differential between the inner chamber 288 of the pressure differentiation device 291 and the ambient pressure or at least reducing the pressure differentiation. The trigger mechanism 289 may include any means known in the art capable of releasing or reducing the pressure differential, including but not limited to any of the sensors or actuators described herein or any component of an actuator or sensor. In embodiments wherein the bodily waste isolation device 290 is adapted to be triggered by urine, the trigger mechanism 289 is preferably disposed in an article such that it will be located where urination is likely to occur (i.e. a urine loading zone) or is operatively associated with a sensor or actuator located in the urine loading zone such that the trigger mechanism will be capable of releasing the vacuum when the wearer urinates or otherwise causes the trigger to activate.

In the embodiment shown in FIGS. 13–13a, the first resilient element 296 preferably comprises a material which provides a low resistance air flux pathway for pressure equilibration once the pressure differential device 291 (e.g. bag 292) is compromised and the vacuum is lost. In one preferred embodiment, the first resilient member includes a macroporous foam, however, other resilient materials such as the resilient materials described above may be suitable. Because the resilient elements 294 and 296 are operatively connected via an open passageway 298 in the pressure differentiation device 291 in the region between the elements, the air passing into the first resilient element 296 can flow toward the second resilient element 294, providing a means for filling the second resilient element 294 and any space around it with air. Accordingly, the second resilient member 294 is able to expand upon dissolution of at least a portion of the bag 292 near the first resilient element 296.

Figures 14, 14A:
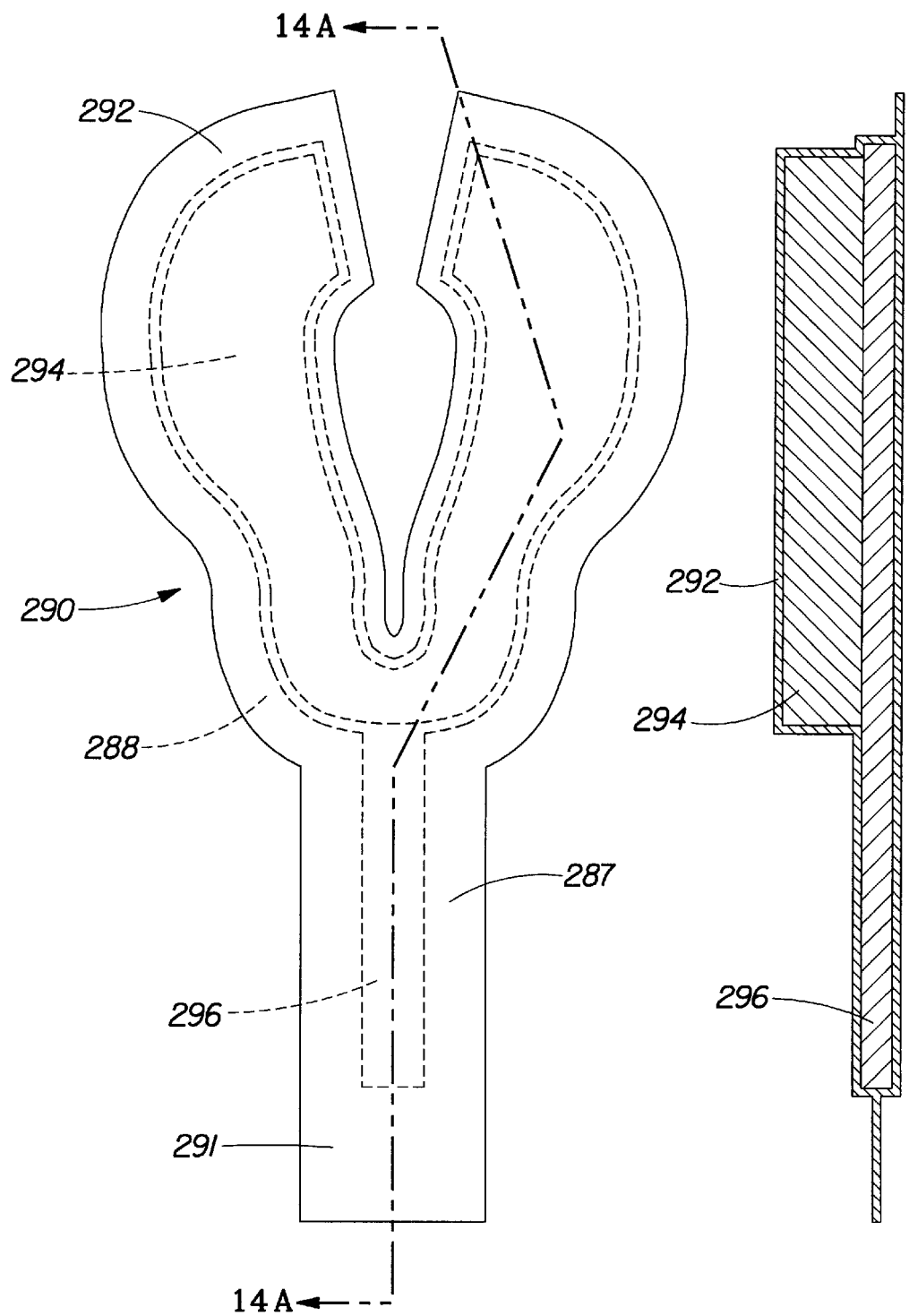

In another embodiment, as shown in FIGS. 14 and 14a, the article of the present invention may include a first resilient element 296 and a second resilient element 294 configured to be abutting one another or at least partially overlapping. The first and second resilient elements are preferably held under vacuum compression in the inner chamber 288 of a pressure differential device 291, as described above. At least a portion of the first resilient member 296 is preferably disposed outwardly from any overlapping portions of the first and second resilient elements. As above, the bodily waste isolation device 290 preferably includes a trigger mechanism 289 which is capable of releasing the pressure differential between the inner chamber 288 of the pressure differentiation device 291 and the ambient pressure or at least reducing the pressure differentiation. The trigger mechanism 289 is preferably disposed in an article such that it will be located where urination is likely to occur (i.e. a urine loading zone) or is operatively associated with a sensor or actuator located in the urine loading zone such that the trigger mechanism will be capable of releasing the vacuum when the wearer urinates or otherwise causes the trigger to activate. When the pressure differential is removed the resilient elements 294 and 296 are able to increase in volume. It has been found to be advantageous to have at least one of the first or second resilient elements to include a material which has openings that easily permit the passage of air and which do not become blocked, for example, by the material of a soluble bag 292 or seal which comprises the pressure differential device 291. In preferred embodiments, such resilient materials may include macroporous foams, however other materials including the resilient materials described above may be suitable.

Figure 15:
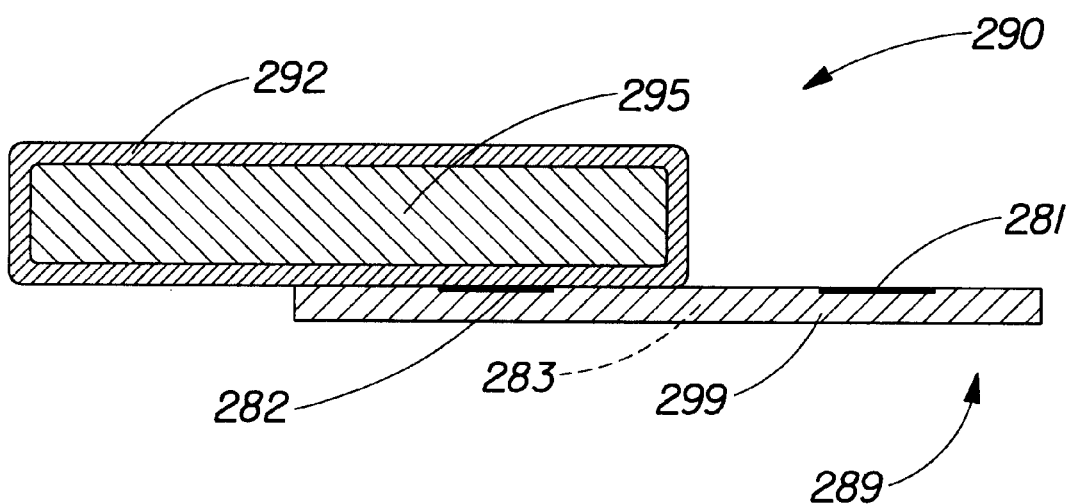
FIG. 15 is a cross-section view of an alternative embodiment of the waste isolation device of the present invention.

In yet another embodiment, as shown in FIG. 15, the article of the present invention may include a trigger 289 comprising a closed system liquid transport member 299, as described above, operatively connected to the bodily waste isolation device 290. The closed system liquid transport member 299 preferably includes an inlet port 281, an outlet port 282 and a liquid 283. The outlet port is preferably disposed adjacent at least a portion of pressure differential device 291, such as a soluble bag 292 or soluble seal. The inlet port 281 is preferably disposed in a different location from the outlet port 282. For example, the inlet port 292 is preferably disposed such that it is located near or at the urine or other discharge zone of the article into which the waste isolation device 290 is in incorporated. Accordingly, when the wearer urinates or otherwise discharges fluid, the fluid is accepted into the inlet port 281. As a result, the closed system liquid transport member 299 releases some liquid from the outlet port 282 which triggers the dissolution at least a portion of the soluble bag 292 or seal. Once dissolved, the pressure differential in the bag is reduced or eliminated and the resilient material 295 is able to expand.

In any of the embodiments of the present invention utilizing a soluble bag, the soluble bag may be soluble in the presence of one or more different types of input, such as water, urine, fecal enzymes, a pH level, etc., and may have physical and/or chemical characteristics (e.g., thickness) that may be designed to set a threshold level of that input required to dissolve the bag. The soluble bag may, for example, comprise a plastic film that is soluble to water such as PVA films supplied by Chris-Craft Industrial Products, Inc. of South Holland, Ill. as MONOSOL M7031, M7030, M8630, M8534, or E6030 film, or H. B. Fuller Company of St. Paul, Minn. as HL 1636 or HL 1669-X. The film thickness, for example, may also be modified to provide a desired activation. The film used may, for example, also have a thickness in the range from about 0.0005 to about 0.0015 inches. An HL 1636 film having a thickness of about 0.001 inches, for example, will activate with a moisture content of about 0.049 grams per square inch.

In some embodiments of the present invention, the bodily waste isolation device may operate as a non-modulating, discontinuous responsive system. For example, if a soluble bag is used, the soluble portion of the bag acts as a sensor that responds to a specific input. The sensor may, for example, be responsive to water in urine or an enzyme in feces. When any soluble portion of the bag contacts a threshold level of urine, fecal moisture, or a fecal enzyme, the soluble portion of the bag dissolves and releases the compression material, which expands to capture, surround or envelop the feces deposited upon the article. The physical and chemical characteristics of the material used to form the bag define the threshold level of the input and act as a controller that determines when the compression material is to be released. When the bag dissolves, the release of vacuum and the expansion of the compression material function as an actuator to capture the bodily waste. Thus, the bodily waste isolation device acts as a one-time discontinuous switch that releases the stored mechanical energy of the compression material when a threshold level of a given input is detected. The useful energy of the responsive system includes: (stored energy)-(hysteresis loss). The compression material used preferably has a minimal hysteresis loss and a maximum recovery. More preferably, the compressive hysteresis loss is less than about 25% so that the recovery upon release is at least about 75%.

The present invention may also comprise an open loop responsive system or a feedback control loop responsive system. In one embodiment, a soluble bag may be used which includes a soluble seal that is located in a portion of the article where the seal will come into contact with urine. If the seal dissolves in urine and the device captures feces, for example, the responsive system comprises an open loop system because the output of the system, i.e., the feces present on the surface of the article and/or adjacent to the skin of the wearer, does not affect the input, i.e., the urine. If the bag responds to fecal moisture or a fecal enzyme, however, the responsive system comprises a feedback control loop because the system uses a measure of the output, i.e., the feces present on the surface of the article and/or adjacent to the skin of the wearer, as the trigger of a function to capture or surround that feces. In this example, the feedback control loop responsive system is non-modulating because it acts as a one time switch and does not continually or repeatedly alter the input to maintain a desired set point level for the output.

In another embodiment of the present invention, a foam such as described in the above example or another resilient material may be twisted creating torsional mechanical potential energy and enclosed in a soluble film envelope, bag or capsule as described above. Preferably, the twisted resilient material is held in the twisted position in the pressure differentiation device under vacuum. In this embodiment, when a threshold level of moisture, pH, etc. is detected the pressure differentiation device is triggered to discontinuously releasing the vacuum and thus, releasing the foam. The stored torsional mechanical potential energy causes the foam to unwind and may perform a responsive function such as storing, capturing or entrapping bodily waste such as feces, urine or menses, wiping the skin of the wearer, applying a skin treatment agent to the skin of the wearer, etc. In this embodiment, the responsive system provides a non-modulating, discontinuous response. If the system acts on something other than the input, e.g., it acts upon the skin of the wearer, the responsive system comprises an open loop system. If, however, the system acts upon the input, e.g., if the trigger responds to fecal moisture or fecal enzymes and the twisted resilient material transports feces via a "corkscrew" action, the system comprises a closed loop system.

In another embodiment, an electrical sensor may detect changes in the electrical activity of the wearer's external anal sphincter muscles to predict an imminent urination and/or defecation, i.e., a proactive sensor. Upon detection of a threshold signal drop in electrical activity of the muscles, the sensor or the controller may, for example, trigger the opening of a valve to release water to dissolve a water soluble portion or seal of a bag that holds a compressed foam in vacuum compression as described above, in preparation to capture waste of the imminent urination and/or defecation. Alternatively, the switch may effect the release or delivery of a skin care composition to treat the skin surface prior to feces contact of the skin. In this embodiment, the responsive system comprises a discontinuous system that responds to the electrical activity of the wearer's external anal sphincter muscle when that electrical activity reaches a threshold signal level. This responsive system also comprises an open loop system because the system is acting upon something other than the electrical activity input signal, i.e., it is acting on the feces or the article.

In yet another embodiment, a responsive system of the present invention may comprise a pH control agent contained within a resilient material such as the foams described above. The resilient material may be constrained under vacuum by a pressure differentiation device including a pH sensitive film that is insoluble, i.e., a solid, below or predefined pH (e.g., less than a pH of about 6.0), but soluble above that pH level. Upon detection of the threshold pH level or above, the film dissolves, releasing the stored compressive potential energy of the resilient material, which delivers the pH control agent. Alternatively, an enzyme inhibitor, a skin care composition, etc. may be contained within the compressed resilient material. The film may alternatively be soluble in the presence of one or more fecal enzymes, water, etc. Exemplary pH sensitive materials are known in the art and include polyacrylamides, phthalate derivatives, formalized gelatin, shellac, keratin, cellulose derivatives, e.g., oxidized cellulose, and polyacrylic acid derivatives. Preferred materials include cellulose acetate phthalate, vinyl acetate, polyvinyl acetate phthalate, hydroxy propyl methyl cellulose phtalate and poly methacrylate blended with acrylic acid and acrylic ester copolymers. Other exemplary materials are described in EP 612, 520 A2 entitled "pH Triggered Osmotic Bursting Delivery Devices", which is incorporated herein by reference.

In the pH sensitive delivery embodiment listed above, the responsive system may comprise either a discontinuous or continuous responsive system having a feedback control loop that acts upon the pH level after a threshold pH level has been reached. These embodiments may be either modulating or non-modulating. If the delivered pH control agent, for example, comprises a buffer that contains both pH increasing and pH decreasing components, the system comprises a modulating feedback control loop system that will continually monitor the pH level in the article and maintain the pH level at a desired set point or within a target range of the buffer whether the pH is raised or lowered. If the responsive system, however, delivers only a pH increasing agent at the first pH threshold level, for example, the system comprises a non-modulating feedback control loop system because the pH decreasing agent will lower the pH of the system until the agent is exhausted and will not maintain the pH of the system at a desired pH level or within a target pH range. If, however, it is known that bodily waste deposited in the article will raise the pH level, and the system deliver a predetermined quantity of a pH decreasing agent each time the pH level in the article reaches a threshold pH level, the system may comprise a modulating feedback control loop system if it will repeatedly release the pH control agent whenever the pH of the article is above the desired set point of the system.

In another embodiment, a sufficient quantity of water containing electrolytes (e.g., from urine or feces) may be detected by an electrical sensor when the electrolytic water completes a circuit, i.e., as a switch, causing current from a stored energy source such as a battery to initiate a mechanical actuator. For example, the current may be applied to an electrically sensitive gel and cause it to change geometry and create void space for feces in the article. Again, this embodiment comprises a discontinuous responsive system that may be an open loop or a feedback control loop system depending upon whether the input sensed is being affected by the responsive system. If the sensor detects moisture in urine, for example, the responsive system that creates a void space for receiving feces comprises an open loop system. If the sensor detects fecal moisture, however, the responsive system comprises a feedback control loop system because it acts upon the input being sensed. In this example, the feedback control loop system may further comprise a modulating system if the void space captures the fecal moisture along with the feces, the moisture evaporates or is drawn away from the sensor element, thereby opening the circuit, and the controller activates another void space when the sensor detects fecal moisture again.

In a further embodiment of the present invention, an absorbent material that swells when absorbing a liquid may be used as a sensor that, when a threshold level of swelling has occurred, mechanically closes a pair of electrical contacts in order to complete an electrical circuit. In this embodiment, the electrical circuit may trigger an actuator in a discontinuous manner to perform a responsive function on the bodily waste, the wearer, the article or any component or components thereof For example, the actuator may open a valve to allow the liquid to flow to another portion of the article, pump the liquid to another portion of the article, initiate a geometric change in an electrically sensitive create a void space, deliver a skin care composition, a pH control agent or a deodorant, etc.

A material such as a fiber, film, nonwoven or other cellular structure may also be restrained in a given configuration by a pressure differentiation device that responds to a bodily waste such as feces, or a component of that bodily waste. When the bodily waste contacts the restraining material, the restraining material may release the fiber, film, nonwoven or other cellular structure to capture or isolate the waste away from the wearer's skin. An elastic barrier, for example, may be restrained at two restraint points away from a void space in an article by a material that dissolves, weakens, etc. in response to urine, fecal moisture or a fecal enzyme. When the feces has been deposited in the void space, and the restraining material at one or both of the restraint points dissolves, the elastic barrier may contract in a discontinuous manner and cover the void space to isolate the feces from the skin of the wearer.

In yet another embodiment, one or more fecal enzymes may be detected by a sensor such as an enzyme-degradable film or capsule, or a biosensor as described above to trigger a separate actuator, e.g., an electrically operated valve, to deliver an enzyme inhibitor to treat the skin. Exemplary enzyme inhibitors are disclosed in U.S. patent application Ser. No. 09/041,266 entitled "Disposable Absorbent Article Having A Skin Care Composition Containing An Enzyme Inhibitor" filed on Mar. 12, 1998, which is incorporated by reference herein. In yet another embodiment, certain pH conditions may be detected by the use of a pH sensitive gel, which may open a valve to deliver a pH control agent to treat the skin. In another embodiment, a pre-defined pressure threshold is detected, resulting in the rupture of a capsule or "bubble," effecting the delivery of a skin care treatment agent or composition. Exemplary skin care compositions (or lotions), are disclosed in U.S. Pat. Nos. 5,607,760 entitled "Disposable Absorbent Article Having A Lotioned Topsheet Containing An Emollient And A Polyol Polyester Immobilizing Agent," issued to Donald C. Roe on Mar. 4, 1997; U.S. Pat. No. 5,609,587 entitled "Diaper Having A Lotioned Topsheet Comprising A Liquid Polyol Polyester Emollient And An Immobilizing Agent," issued to Donald C. Roe on Mar. 11, 1997; U.S. Pat. No. 5,635,191 entitled "Diaper Having A Lotioned Topsheet Containing A Polysiloxane Emollient," issued to Donald C. Roe et al. on Jun. 3, 1997; and U.S. Pat. No. 5,643,588 entitled "Diaper Having A Lotioned Topsheet" issued to Donald C. Roe et al. on Jul. 1, 1997, as well as U.S. patent applications Ser. Nos. 08/926, 532 and 08/926,533, each filed on Sep. 10, 1997, each of the above listed patents and applications are incorporated herein by reference.

While particular non-limiting embodiments and examples and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention. Also, although the present invention is illustrated and described primarily with respect to a disposable diaper, the present invention is not limited to this embodiment. The present invention may also be used, for example, in articles that are applied directly to a wearer prior to the application of a disposable diaper or in place of a disposable diaper, in a pull-on diaper, a diaper insert, a sanitary napkin, a tampon, etc. It is therefore intended to cover in the appended claims all such changes and modifications that are within the scope of this invention.

What is claimed is:

1. A disposable article to be fitted to a wearer comprising:
   a bodily waste isolation device including:
      a pressure differentiation device having an exterior and at least one inner chamber, the pressure differentiation device maintaining the inner chamber at a pressure lower than an ambient pressure; and
      at least two resilient elements with different properties disposed in the inner chamber of the pressure differentiation device and held under vacuum compression.

2. The disposable article of claim 1 wherein at least a portion of the exterior of the pressure differentiation device includes a water soluble film.

3. The disposable article of claim 1 further comprising a trigger mechanism capable of increasing the lower pressure of the inner chamber.

4. The disposable article of claim 3 wherein the trigger mechanism is selected from the group of a sensor, an actuator, or a combination thereof.

5. The disposable article of claim 4 wherein the sensor is selected from the group of: an electrical sensor, a mechanical sensor, a chemical sensor, a biosensor, a water soluble film, and a water soluble pH sensitive film.

6. The disposable article of claim 5 wherein the controller is operatively connected to the sensor.

7. The disposable article of claim 4 further comprising a controller, the controller being adapted to receive a signal from the sensor and to allow an actuator to perform a responsive function when a threshold level of an input has been met.

8. The disposable article of claim 3 wherein the article includes a urine loading zone into which the wearer urinates, at least a portion of the trigger mechanism being disposed at least partially in the urine loading zone.

9. The disposable article of claim 1 wherein the resilient elements are at least partially overlapping each other.

10. The disposable article of claim 1 wherein the resilient elements are disposed in a non-touching configuration.

11. The disposable article of claim 1 wherein at least one of the resilent elements comprises a microporous foam.

12. The disposable article of claim 1 wherein at least one of the resilient elements comprises a macroporous foam.

13. The disposable article of claim 1 wherein at least one of the resilient elements enhances air flux into the inner chamber of the pressure differentiation device.

14. The disposable article of claim 1 wherein at least one of the resilient elements includes a microporous component and at least one of the resilient elements includes a macroporous component, the macroporous component overlapping at least a part of the microporous component.

15. The disposable article of claim 1 wherein at least one of the resilient elements includes a microporous component and at least one of the resilient elements includes a macroporous component, the macroporous component being operatively connected to the microporous component.

16. The disposable article of claim 1 wherein at least one of the resilient elements includes at least one feces receiving aperture.

17. The disposable article of claim 16 wherein the feces receiving aperture provides a volume of at least 20 cubic centimeters under an applied pressure of about 0.1 psi.

18. The disposable article of claim 1 wherein at least one of the resilient elements compresses no more than about 25% under an applied pressure of about 0.1 psi.

19. The disposable article of claim 1 further including a feedback control loop in which a controller is adapted to allow the resilient elements to perform a responsive function when the vacuum released.

20. The disposable article of claim 1, wherein the bodily waste isolation device performs a responsive function including one or more of the following: transforming potential energy into kinetic energy, delivering a stored material, delivering an active ingredient, delivering a stored material to the skin of a wearer, delivering a stored material to a bodily waste, entrapping feces, encapsulating feces, providing a void space, and pumping a fluid bodily waste.

21. The disposable article of claim 1, wherein the article selected from the group of: a diaper, a training pant, a sanitary napkin, a tampon, a colostomy bag, an insert and a waste bag.

22. A disposable absorbent article to be fitted to a wearer having a front region, a back region and a central region disposed between the front region and the back region, the article comprising:
   a topsheet;
   a backsheet joined with the topsheet;
   an absorbent core disposed between the topsheet and the backsheet; and
   a bodily waste isolation device including:
      a pressure differentiation device having an exterior and at least one inner chamber, the pressure differentiation device maintaining the inner chamber at a pressure lower than an ambient pressure;
      at least two resilient elements with different properties disposed in the inner chamber of the pressure differentiation device and held under vacuum compression; and
      a trigger mechanism capable of increasing the pressure of the inner chamber.

23. The disposable article of claim 22 wherein at least a portion of the exterior of the pressure differentiation device includes a water soluble film.

24. The disposable article of claim 22 wherein the trigger mechanism is selected from the group of a sensor or an actuator.

25. The disposable article of claim 24 wherein the sensor is selected from the group of: an electrical sensor, a mechanical sensor, a chemical sensor, a biosensor, a water soluble film, a water soluble pH sensitive film, and a closed system liquid transport member.

26. The disposable article of claim 22 wherein the resilient elements are at least partially overlapping each other.

27. The disposable article of claim 22 wherein the article includes a urine loading zone into which the wearer urinates, at least a portion of the trigger mechanism being disposed at least partially in the urine loading zone.

28. The disposable article of claim 22 wherein at least one of the resilient elements includes a microporous component and at least one of the resilient elements includes a macroporous component.

29. The disposable article of claim 22 wherein at least one of the resilient elements includes at least one feces receiving aperture.

30. The disposable article of claim 29 wherein the feces receiving aperture provides a volume of at least 20 cubic centimeters under an applied pressure of about 0.1 psi.

31. The disposable article of claim 22 wherein at least one of the resilient elements compresses no more than about 25% under an applied pressure of about 0.1 psi.

* * * * *